(12) United States Patent
Forney et al.

(10) Patent No.: US 7,627,437 B2
(45) Date of Patent: Dec. 1, 2009

(54) CATEGORIZATION OF MICROBIAL COMMUNITIES

(75) Inventors: Larry J. Forney, Troy, ID (US); James Foster, Potlatch, ID (US); Celeste Brown, Moscow, ID (US); Paul Joyce, Moscow, ID (US); Zaid Abdo, Pullman, WA (US); Audra Johnson, Moscow, ID (US); Xia Zhou, Pullman, WA (US)

(73) Assignee: Idaho Research Foundation, Moscow, ID (US)

( * ) Notice: Subject to any disclaimer, the term of this patent is extended or adjusted under 35 U.S.C. 154(b) by 0 days.

(21) Appl. No.: 11/331,856

(22) Filed: Jan. 12, 2006

(65) Prior Publication Data

US 2006/0172330 A1 Aug. 3, 2006

Related U.S. Application Data

(60) Provisional application No. 60/644,080, filed on Jan. 14, 2005.

(51) Int. Cl.
*G01N 33/48* (2006.01)
*C12Q 1/68* (2006.01)

(52) U.S. Cl. .................................. 702/19; 435/6
(58) Field of Classification Search ................. None
See application file for complete search history.

(56) References Cited

U.S. PATENT DOCUMENTS

| 6,180,100 | B1 | 1/2001 | Bruce |
| 2004/0022775 | A1 | 2/2004 | Reid et al. |
| 2004/0126369 | A1 | 7/2004 | Payne |
| 2005/0026188 | A1* | 2/2005 | Van Kessel et al. ............ 435/6 |

OTHER PUBLICATIONS

Coolen et al. Characterization of the microbial flora of the human vulva by analysis of terminal restriction fragment polymorphism (T-RFLP) of 16s rDNA genes. Abstracts of the General Meeting of the American Society for Microbiology. vol. 101, p. 262 (2001).*
Moore et al. Human fecal Flora: The Normal Flora of 20 Japanese-Hawaiians Applied Microbiology vol. 27, pp. 961-979 (1974).*
Moore et al. 95 Intestinal Floras of Populations That Have a High Risk of Colon Cancer Applied and Environmental Microbiology vol. 61 pp. 3202-3207 (1995).*
Abdo et al., "Statistical methods for characterizing diversity of microbial communities by analysis of terminal restriction fragment length polymorphisms of 16S rRNA genes," *Environ. Microbiol.*, 8(5):929-938, 2006.
Antonio et al., "The Identification of Vaginal *Lactobacillus* Species and the Demographic and Microbiologic Characteristics of Women Colonized by These Species," *J. Infect. Dis.*, 180:1950-1956, 1999.
Bergeron et al., "New DNA-based PCR approaches for rapid real-time detection and prevention of group B streptococcal infections in newborns and pregnant women," *Exp. Rev. Mol. Med.*, (01)00380-5a.pdf, Nov. 8, 2001.

Burton et al., "Evaluation of the Bacterial Vaginal Flora of 20 Postmenopausal Women by Direct (Nugent Score) and Molecular (Polymerase Chain Reaction and Denaturing Gradient Gel Electrophoresis) Techniques," *J. Infect. Dis.*, 186:1770-1780, 2002.
Burton et al., "Improved Understanding of the Bacterial Vaginal Microbiota of Women before and after Probiotic Instillation," *Appl. Enviro. Microbiol.*, 69(1):97-101, 2003.
Burton et al., "Detection of *Atopobium vaginae* in Postmenopausal Women by Cultivation-Independent Methods Warrants Further Investigation," *J. Clin. Microbiol.*, 42(4):1829-1831, 2004.
Cadieux et aL, "*Lactobacillus* strains and vaginal ecology," *JAMA*, 287(15):1940-1941, 2002.
Chang et al., "Inhibition of HIV infectivity by a natural human isolate of *Lactobacillus jensenii* engineered to express functional two-domain CD4," *PNAS*, 100(20):11672-11677, 2003.
Cole et al., "The Ribosomal Database Project (RDP-II): previewing a new autoaligner that allows regular updates and the new prokaryotic taxonomy," *Nucl. Acids Res.*, 31(1):442-443, 2003.
Cook et al., "Clinical, Microbiological, and Biochemical Factors in Recurrent Bacterial Vaginosis," *J. Clin. Microbiol.*, 30(4):870-877, 1992.
Coolen et al., "Characterization of Microbial Communities Found in the Human Vagina by Analysis of Terminal Restriction Fragment Length Polymorhisms of 16S rRNA Genes," *Appl. Env. Microbiol.*, 71(12):8729-8737, 2005.
Delaney et al., "Nugent Score Related to Vaginal Culture in Pregnant Women," *The Am. College of Obstet. And Gynecol.*, 98(1):79-84, 2001.
Engebretson et al., "Fidelity of Select Restriction Endonucleases in Determining Microbial Diversity by Terminal-Restriction Fragment Length Polymorphism," *Appl. Environ. Microbiology*, 69(8):4823-4829, 2003.
Eschenbach et al., "Prevalence of Hydrogen Peroxide-Producing *Lactobacillus* Species in Normal Women and Women with Bacterial Vaginosis," *J. Clin. Microbiol.*, 27(2):251-256, 1989.
Eschenbach et al., "Influence of the Normal Menstrual Cycle on Vaginal Tissue, Discharge, and Microflora ," *Clin. Infect. Dis.*, 30:901-907, 2000.
Ezaki et al., "Proposal of the genera *Anaerococcus* gen. nov., *Peptoniphilus* gen. nov. And *Gallicola* gen. nov. For members of the genus *Peptostreptococcus*," *Int. J. Syst. Evol. Microbiol.*, 51:1521-1528, 2001.
Falsen et al., "Phenotypic and phylogenetic characterization of a novel *Lactobacillus* species from human source: description of *Lactobacillus iners* sp. nov.," *Int. J. Syst. Bacteriol.*, 49:217-221, 1999.

(Continued)

*Primary Examiner*—John S Brusca
(74) *Attorney, Agent, or Firm*—Klarquist Sparkman, LLP

(57) ABSTRACT

The present disclosure provides methods for defining one or more microbial communities. In an example, the method can include providing a plurality of microbial profiles, wherein each microbial profile is established from a sample of microorganisms obtained from an individual subject. The method can also include identifying one or more consensus profiles from among the plurality of microbial profiles. These methods can be used to characterize normal and pathological microflora in vaginal samples.

32 Claims, 4 Drawing Sheets

OTHER PUBLICATIONS

Favier et al., "Molecular Monitoring of Succession of Bacterial Communities in Human Neonates," *App. Environ. Microbiol.*, 68(1):219-226, 2002.

Ferris et al., "Use of Species-Directed 16S rRNA Gene PCR Primers for Detection of *Atopobium vaginae* in Patients with Bacterial Vaginosis," *J. Clin. Microbiol.*, 42(12):5892-5894, 2004.

Forney et al., "Molecular microbial ecology: land of the one-eyed king," *Curr. Opin. Microbiology*, 7:210-220, 2004.

Forney et al., "The vaginal flora of healthy women is not always dominated by lactobacillus species," *J. Infec. Dis.*, 194(10):1468-9, 2006.

Frank et al., "Culture-Independent Molecular Analysis of Microbial Constituents of the Healthy Human Outer Ear," *J. Clin. Microbiol.*, 41(1):295-303, 2003.

Gupta et al., "Inverse association of $H_2O_2$-producing Lactobacilli and vaginal *Escherichia coli* colonization in women with recurrent urinary tract infections," *J. Infect. Dis.*, 178:446-450, 1998.

Gupta et al. "Effects of Contraceptive Method on the Vaginal Microbial Flora: A Prospective Evaluation," *J. Infect. Dis.*, 181:595-601, 2000.

Hay, P.E., "Bacterial vaginosis and miscarriage," *Curr. Opin. Infect. Dis.*, 17:41-44, 2004.

Hilton et al., "*Lactobacillus* GG Vaginal Suppositories and Vaginitis," *J. Clin. Microbiol.*, 33(5):1433, 1995.

Ison et al., "Validation of a simplified grading of Gram stained vaginal smears for use in genitourinary medicine clinics," *Sex. Transm. Infect.*, 78:413-415, 2002.

Jovita et al., "Characterization of a Novel *Atopobium* Isolate from the Human Vagina: Description of *Atopobium vaginae* sp. nov.," *Int. J. Syst. Bacteriol.*, 49:1573-1576, 1999.

Jukes et al., "Evolution of Protein Molecules," *Mammalian Protein Metabolism*, Academic Press, Inc., New York and London, 1969.

Kazor et al., "Diversity of Bacterial Populations on the Tongue Dorsa of Patients with Halitosis and Healthy Patients," *J. Clin. Micrbiol.*, 41(2):558-563, 2003.

Kitts, C.L., "Terminal restriction fragment patterns: a tool for comparing microbial communities and assessing community dynamics," *Curr. Issues Infest. Microbiol.*, 2(1):17-25, 2001.

Klebanoff et al., "Viricidal Effect of *Lactobacillus acidophilus* on Human Immunodeficiency Virus Type 1: Possible Role in Heterosexual Transmission," *J. Exp. Med.*, 174:289-292, 1991.

Kroes et al., "Bacterial diversity within the human subgingival crevice," *PNAS*, 96(25):14547-14552, 1999.

Larsen et al., "Understanding the Bacterial Flora of the Female Genital Tract," *Clin. Infect. Dis.*, 32:e69-e77, 2001.

Lindner et al., "Quantitative studies of the vaginal flora of healthy women and of obstetric and gynaecological patients," *J. Med. Microbiol.*, 11:233-241, 1978.

Liu et al., "Characterization of Microbial Diversity by Determining Terminal Restriction Fragment Length Polymorphisms of Genes Encoding 16S rRNA," *Appl. Env. Microbiol.*, 63(11):4516-4522, 1997.

Martin et al., "Vaginal Lactobacilli, Microbial Flora, and Risk of Human Immunodeficiency Virus Type 1 and Sexually Transmitted Disease Acquisition," *J. Infect. Dis.*, 180:1863-1868, 1999.

Masfari et al., "Quantitative studies of vaginal bacteria," *Genitourin Med.*, 62:256-263, 1986.

Massi et al., "Identification method based on PCR combined with automated ribotyping for tracking probiotic *Lactobacillus* strains colonizing the human gut and vagina," *J. Appl. Microbiol.*, 96:777-786, 2004.

McClean et al., "Characterization and selection of a *Lactobacillus* species to re-colonize the vagina of women with recurrent bacterial vaginosis," *J. Med. Microbiol.* 49:543-552, 2000.

Milligan et at, "An Examination of Procedures for Determining the Number of Clusters in a Data Set," *Psychometrika*, 50(2):159-179, 1985.

Newton et al., "Predictors of the vaginal microflora," *Am. J. Obstet. Gynecol.*, 184(5):845-855, 2001.

Nugent et al., "Reliability of Diagnosing Bacterial Vaginosis is Improved by a Standardized Method of Gram Stain Interpretation," *J. Clin. Microbiol.*, 29:297-301, 1991.

O'Dowd et al., "Evaluation of a rapid diagnostic test for bacterial vaginosis," *Br. J. Obstet. Gynaecol.*, 103:366-370, 1996.

Oda et al., "Genotypic and Phenotypic Diversity within Species of Purple Nonsulfur Bacteria Isolated from Aquatic Sediments," *Appl. Env. Microbiol.*, 68(7)3467-3477, 2002.

Oda et al., "Biogeography of the Purple NonSulfur Bacterium *Rhodopseudomonas palustris*," *Appl. Env. Microbiol.*, 69(9):5186-5191, 2003.

Osborn et al., "An evaluation of terminal-restriction fragment length polymorphism (T-RFLP) analysis for the study of microbial community structure and dynamics," *Environ. Microbiol.*, 2(1):39-50, 2002.

Ouwehand et al., "Probiotics: an overview of beneficial effects," *Antonie van Leeuwenhoek*, 82:279-289, 2002.

Paster et al., "Bacterial Diversity in Human Subgingival Plaque," *J. Bacteriol.*, 183(12):3770-3783, 2001.

Pavlova et al., "Genetic diversity of vaginal lactobacilli from women in different countries based on 16S rRNA gene sequences," *J. Appl. Microbiol.*, 92(3):451-459, 2002.

Pei et al., "Bacterial biota in the human distal esophagus," *PNAS*, 101(12):4250-4255, 2004.

Pybus et al., "Microbial interactions in the vaginal ecosystem, with emphasis on the pathogenesis of bacterial vaginosis," *Microbes Infect.*, 1:285-292, 1999.

Redondo-Lopez et al., "Emerging Role of Lactobacilli in the Control and Maintenance of the Vaginal Bacterial Microflora," *Rev. Infect. Dis.*, 12(5):856-872, 1990.

Reid et at., "Identification and plasmid profiles of *Lactobacillus* species from the vagina of 100 healthy women," *FEMS. Immunol. Med. Microbiol.*, 15:23-26, 1996.

Reid et al., "Urogenital Lactobacilli Probiotics, Reliability, and Regulatory Issues," *J. Dairy Sci.*, 84:E164-E169, 2001.

Reid et al., "Oral use of *Lactobacillus rhamnosus* GR-1 and *L. fermentum* RC-14 significantly alters vaginal flora: randomized, placebo-controlled trial in 64 healthy women," *FEMS Immunol. Med. Microbiol.*, 35:131-134, 2003.

Saitou et al., "The Neighbor-joining Method: A New Method for Reconstructing Phylogenetic Trees," *Mol. Biol. Evol.*, 4(4):406-425, 1987.

Schwebke, J.R., "Bacterial Vaginosis," *Curr. Infect. Dis. Rep.*, 2:14-17, 2000.

Seiber et al., "*Lactobacillus acidophilus* and yogurt in the prevention and therapy of bacterial vaginosis," *Int. Daily J.* 8:599-607, 1998.

Sobel, J.D., "Bacterial Vaginosis," *Annu. Rev. Med.*, 51:349-356, 2000.

Tärnberg et al. "Identification of randomly selected colonies of lactobacilli from normal vaginal fluid by pyrosequencing of the 16S rDNA variable V1 and V3 regions," *APMIS*, 110:802-810, 2002.

Thompson et al., "Clustal W: improving the sensitivity of progressive multiple sequence alignment through sequence weighting, position-specific gap penalties and weight matrix choice," *Nucleic Acids Research*, 22(22):4673-4680, 1994.

Vasquez et al., "Vaginal *Lactobacillus* Flora of Healthy Swedish Women," *J. Clin. Microbiol.*, 40(8):2746-2749, 2002.

Ventura et al., "Analysis, Characterization, and Loci of the *tuf* Genes in *Lactobacillus* and *Bifidobacterium* Species and Their Direct Application for Species Identification," *Appl. Environ. Microbiol.*, 69(11):6908-6922, 2003.

Verhelst et al., "Cloning of 16S rRNA genes amplified from normal and disturbed vaginal microflora suggests a strong association between *Atopobium vaginae*, *Gardnerella vaginalis* and bacterial vaginosis," *BMC Microbiology*, 4:11 pages, Apr. 21, 2004.

Wilks et al, "Quantitative bacteriology of the vaginal flora during the menstrual cycle," *J. Med. Microbiol.*, 24:241-245, 1987.

Wolrath et al., "Analysis of Bacterial Vaginosis-Related Amines in Vaginal Fluid by Gas Chromatography and Mass Spectrometry," *J. Clin. Microbiol.*, 39(11):4026-4031, 2001.

Yu et al., "Estimation of sample size and assurance probability in library screening," *Biotechniques*, 10(6):776-777, 1991.

Zhong et al., "Differentiation of *Lactobacillus* Species by Molecular Typing," *Appl. Environ. Microbiology*, 64(7):2418-2423, 1998.

Zhou et al., "Characterization of vaginal microbial communities in adult healthy women using cultivation-independent methods," *Microbiology*, 150:2565-2573, 2004.

Ziola et al., "Serogroups of the beer spoilage bacterium *Megasphaera cerevisiae* correlate with the molecular weight of the major EDTA-extractable surface protein," *Can. J. Microbiol.*, 46:95-100, 1999.

Zoetendal et al., "Molecular ecological analysis of the gastrointestinal microbiota: a review," *J. Nutr.*, 134(2):465-472, 2004.

Amsel et al., "Nonspecific vaginitis. Diagnostic criteria and microbial and epidemiological associations," *Am. J. Med.*, 74:14-22, 1983.

Bartlett et al., Quantitative bacteriology of the vaginal flora, *J. Infect. Dis.*, 136:271-277, 1977.

Francesca et al., "Quantitative and qualitative determination of the vaginal microbial flora by real time PCR," *Microbicides*, 2004 (abstract only).

Hawes et al., "Hydrogen peroxide-producing *Lactobacilli* and acquisition of vaginal infections," *J. Infect. Dis.*, 174:1058-1063, 1996.

Hughes and Hillier, "Microbiologic characteristics of Lactobacillus products used for colonization of the vagina," *Obstet. Gynecol.*, 75:244-248, 1990.

Jovita et al., "Characterization of a novel *Atopobium* isolate from the human vagina: description of *Atopobium vaginae* sp. nov.," *Int. J. Syst. Bacteriol.*, 49:1573-1576, 1999.

Marrazzo, J., "Bacterial vaginosis," *Curr. Treat. Opt. Infect. Dis.* 5:63-68, 2003.

Schmid, G.P., "The epidemiology of bacterial vaginosis," *Int. J. Gynaecol. Obstet.*, 67:S17-820, 1999.

Schwebke, J.R., "Diagnostic method for bacterial vaginosis," *Int. J. Gynaecol. Obstet.*, 67:S21-S23, 1999.

Silvester and Dicks, "Identification of lactic acid bacteria isolated from human vaginal secretions," *Antonie van Leeuwenhoek*, 83:117-123, 2003.

\* cited by examiner

SEQUENCE LISTING

<160> NUMBER OF SEQ ID NOS: 23

<210> SEQ ID NO 1

```
<211> LENGTH: 20
<212> TYPE: DNA
<213> ORGANISM: Artificial Sequence
<220> FEATURE:
<223> OTHER INFORMATION: Forward primer 8f
<220> FEATURE:
<221> NAME/KEY: misc_feature
<222> LOCATION: (12)..(12)
<223> OTHER INFORMATION: "m" equals a or c

<400> SEQUENCE: 1
agagtttgat cmtggctcag                                          20

<210> SEQ ID NO 2
<211> LENGTH: 17
<212> TYPE: DNA
<213> ORGANISM: Artificial Sequence
<220> FEATURE:
<223> OTHER INFORMATION: Forward primer 341f

<400> SEQUENCE: 2
cctacgggag gcagcag                                             17

<210> SEQ ID NO 3
<211> LENGTH: 20
<212> TYPE: DNA
<213> ORGANISM: Artificial Sequence
<220> FEATURE:
<223> OTHER INFORMATION: Reverse primer 926r
<220> FEATURE:
<221> NAME/KEY: misc_feature
<222> LOCATION: (15)..(15)
<223> OTHER INFORMATION: "r" equals a or g

<400> SEQUENCE: 3
ccgtcaattc ctttragttt                                          20

<210> SEQ ID NO 4
<211> LENGTH: 15
<212> TYPE: DNA
<213> ORGANISM: Artificial Sequence
<220> FEATURE:
<223> OTHER INFORMATION: Reverse primer 1406r
<220> FEATURE:
<221> NAME/KEY: misc_feature
<222> LOCATION: (14)..(14)
<223> OTHER INFORMATION: "r" equals a or g

<400> SEQUENCE: 4
acgggcggtg tgtrc                                               15

<210> SEQ ID NO 5
<211> LENGTH: 20
<212> TYPE: DNA
<213> ORGANISM: Artificial Sequence
<220> FEATURE:
<223> OTHER INFORMATION: Forward primer 49f
<220> FEATURE:
<221> NAME/KEY: misc_feature
<222> LOCATION: (2)..(2)
<223> OTHER INFORMATION: "n" equals a, c, g or t
<220> FEATURE:
<221> NAME/KEY: misc_feature
<222> LOCATION: (4)..(4)
<223> OTHER INFORMATION: "n" equals a, c, g or t
<220> FEATURE:
<221> NAME/KEY: misc_feature
<222> LOCATION: (17)..(17)
<223> OTHER INFORMATION: "r" equals a or g
<220> FEATURE:
<221> NAME/KEY: misc_feature
```

```
<222> LOCATION: (18)..(18)
<223> OTHER INFORMATION: "r" equals a or g

<400> SEQUENCE: 5
tnanacatgc aagtcgrrcg                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for Atopobium vaginae

<400> SEQUENCE: 6
ttctgctcgc gcagtagcag                                               20

<210> SEQ ID NO 7
<211> LENGTH: 18
<212> TYPE: DNA
<213> ORGANISM: Artificial Sequence
<220> FEATURE:
<223> OTHER INFORMATION: Reverse primer for Atopobium

<400> SEQUENCE: 7
ctcctgacct aacagacc                                                 18

<210> SEQ ID NO 8
<211> LENGTH: 20
<212> TYPE: DNA
<213> ORGANISM: Artificial Sequence
<220> FEATURE:
<223> OTHER INFORMATION: Forward primer for Megasphaera

<400> SEQUENCE: 8
tcttaaaagt gcggggctta                                               20

<210> SEQ ID NO 9
<211> LENGTH: 24
<212> TYPE: DNA
<213> ORGANISM: Artificial Sequence
<220> FEATURE:
<223> OTHER INFORMATION: Reverse primer for Gardnerella vaginalis

<400> SEQUENCE: 9
agacggctcc atcccaaaag ggtt                                          24

<210> SEQ ID NO 10
<211> LENGTH: 22
<212> TYPE: DNA
<213> ORGANISM: Artificial Sequence
<220> FEATURE:
<223> OTHER INFORMATION: Forward primer for Enteric bacteria

<400> SEQUENCE: 10
gcggtccggc cgggaactca aa                                            22

<210> SEQ ID NO 11
<211> LENGTH: 20
<212> TYPE: DNA
<213> ORGANISM: Artificial Sequence
<220> FEATURE:
<223> OTHER INFORMATION: Reverse primer for Enteric bacteria

<400> SEQUENCE: 11
catctgggca catccgatgg                                               20
```

<210> SEQ ID NO 12
<211> LENGTH: 20
<212> TYPE: DNA
<213> ORGANISM: Artificial Sequence
<220> FEATURE:
<223> OTHER INFORMATION: Forward primer for Leptotrichia

<400> SEQUENCE: 12
tgtagactgg gataacagag                                        20

<210> SEQ ID NO 13
<211> LENGTH: 20
<212> TYPE: DNA
<213> ORGANISM: Artificial Sequence
<220> FEATURE:
<223> OTHER INFORMATION: Forward primer for Streptococcus

<400> SEQUENCE: 13
agagtttgat cctggctcag                                        20

<210> SEQ ID NO 14
<211> LENGTH: 24
<212> TYPE: DNA
<213> ORGANISM: Artificial Sequence
<220> FEATURE:
<223> OTHER INFORMATION: Reverse primer for Streptococcus

<400> SEQUENCE: 14
gtaccgtcac attgtgaatt ttcc                                   24

<210> SEQ ID NO 15
<211> LENGTH: 21
<212> TYPE: DNA
<213> ORGANISM: Artificial Sequence
<220> FEATURE:
<223> OTHER INFORMATION: Forward primer for Staphylococcus

<400> SEQUENCE: 15
taactgtaca cgtcttgacg g                                      21

<210> SEQ ID NO 16
<211> LENGTH: 26
<212> TYPE: DNA
<213> ORGANISM: Artificial Sequence
<220> FEATURE:
<223> OTHER INFORMATION: Forward primer for Mycoplasma

<400> SEQUENCE: 16
gtaatacata ggtcgcaagc gttatc                                 26

<210> SEQ ID NO 17
<211> LENGTH: 25
<212> TYPE: DNA
<213> ORGANISM: Artificial Sequence
<220> FEATURE:
<223> OTHER INFORMATION: Reverse primer for Mycoplasma

<400> SEQUENCE: 17
caccatctgt cactctgtta acctc                                  25

<210> SEQ ID NO 18
<211> LENGTH: 26
<212> TYPE: DNA
<213> ORGANISM: Artificial Sequence
<220> FEATURE:
<223> OTHER INFORMATION: Forward primer for Mycoplasma genitalium

```
<400> SEQUENCE: 18
gtaatacata ggtcgcaagc gttatc                                              26

<210> SEQ ID NO 19
<211> LENGTH: 19
<212> TYPE: DNA
<213> ORGANISM: Artificial Sequence
<220> FEATURE:
<223> OTHER INFORMATION: Reverse primer for Mycoplasma genitalium

<400> SEQUENCE: 19
tcggagcgat cccttcggt                                                      19

<210> SEQ ID NO 20
<211> LENGTH: 26
<212> TYPE: DNA
<213> ORGANISM: Artificial Sequence
<220> FEATURE:
<223> OTHER INFORMATION: Forward primer for Mycoplasma hominis

<400> SEQUENCE: 20
gtaatacata ggtcgcaagc gttatc                                              26

<210> SEQ ID NO 21
<211> LENGTH: 22
<212> TYPE: DNA
<213> ORGANISM: Artificial Sequence
<220> FEATURE:
<223> OTHER INFORMATION: Reverse primer for Mycoplasma hominis

<400> SEQUENCE: 21
gacactagca aactagagtt ag                                                  22

<210> SEQ ID NO 22
<211> LENGTH: 20
<212> TYPE: DNA
<213> ORGANISM: Artificial Sequence
<220> FEATURE:
<223> OTHER INFORMATION: Reverse primer for Lactobacillus iners

<400> SEQUENCE: 22
actggggtga agtcgtaaca                                                     20

<210> SEQ ID NO 23
<211> LENGTH: 20
<212> TYPE: DNA
<213> ORGANISM: Artificial Sequence
<220> FEATURE:
<223> OTHER INFORMATION: Forward primer for Lactobacillus crispatus

<400> SEQUENCE: 23
ccggataaga aagcagatcg                                                     20
```

CATEGORIZATION OF MICROBIAL COMMUNITIES

CROSS REFERENCE TO RELATED APPLICATION

This application claims priority to and benefit of U.S. provisional application No. 60/644,080, filed Jan. 14, 2005, which is incorporated herein in its entirety for all purposes.

ACKNOWLEDGEMENT OF GOVERNMENT SUPPORT

The invention was funded in part by the United States Department of Health under grant P20 RR016448. The United States Government has certain rights to the invention.

FIELD OF THE DISCLOSURE

This disclosure relates to the field of microbial ecology. More specifically, the disclosure relates to methods for identifying and categorizing populations of microbiota.

BACKGROUND

Bacterial vaginosis (BV) is the most prevalent cause of vaginitis among women of childbearing age (Holmes et al., *Sexually Transmitted Diseases* (1999)). The prevalence of BV in women varies depending on the population studied, but ranges from 4% to >50%. The occurrence of BV is associated with an increased risk of acquiring sexually transmitted diseases (STDs) including HIV (Martin et al., *J Infect Dis* 178: 1053-1059 (1998); Schmid et al., *Sex Transm Infect* 76:3-4 (2000); Taha et al., *AIDS* 12:1699-1706 (1998); Sobel, *Annu Rev Med* 51:349-356 (2000); Schwebke, *Curr Infect Dis Rep* 2:14-17 (2000); Gupta et al., *J Infect Dis* 178:446-450 (1998); Hawes et al., *J Infect Dis* 174:1058-1063 (1996)), as well as preterm infertility (Sweet, *Infect Dis Obstet Gynecol* 8:184-190 (2000)), delivery of low birth weight infants (Hillier et al., *N Engl J Med* 333:1737-1742 (1995)), spontaneous abortion (Leitich et al., *Am J Obstet Gynecol* 189:139-147 (2003); Ralph et al., *BMJ* 319:220-223 (1999)), pelvic inflammatory disease, and various postoperative infections (Sobel, *Annu Rev Med* 51:349-356 (2000); Pybus & Onderdonk, *Microbes Infect* 1:285-292 (1999), and references therein).

The etiology of BV is complex and poorly understood (Sobel, *Annu Rev Med* 51:349-356 (2000)). It is commonly thought that BV results from replacement of the normal hydrogen peroxide-producing *Lactobacillus* sp. in the vagina with high numbers of *Gardnerella vaginalis, Mycoplasma hominis,* and *Mobiluncus* sp. (Pybus & Onderdonk, *Microb. Ecol. Health Dis.* 9:19-26 (1996); Workowski & Levine, *Sexually Transmitted Diseases Treatment Guidelines,* on the world wide web at cdc.gov/mmwr/preview/mmwrhtml/rr5106a.1.htm). This in turn leads to the development of an oxygen-depleted environment that facilitates the growth of strict anaerobes including Gram-negative species of *Prevotella, Porphyromonas, Bacteroides,* as well as *Peptostreptococcus* (Sobel, *Annu. Rev. Med.* 51:349-356 (2000)), and to higher cytokine levels in the cervix and vagina (Hay et al., *Brit. Med. J.* 308:295-298 (1994); McGregor et al., *Am. J. Obstet. Gynecol.* 170:1048-1060 (1994)). The cause(s) that trigger the depopulation of lactobacilli, changes in microbial community structure, and the overgrowth of other organisms are not fully understood. However, an increased incidence of BV is known to be positively correlated with multiple sex partners, the frequency of intercourse, and douching (Simpson et al., *J. Pediatr. Adolesc. Gynecol.* 17:249-255 (2004)). Since the development of BV has not been attributed to the presence or absence of any single bacterial taxon it is commonly diagnosed based on the existence of three of the following four symptoms: (a) thin homogeneous malodorous discharge; (b) vaginal pH fluid >4.5; (c) an amine odor from vaginal fluid when 10% KOH is added; and (d) the presence of "clue" cells (vaginal epithelial cells with adherent bacteria that obscure cell margins) (Amsel et al., *Am. J. Med.* 74:14-22 (1983)). Alternatively, the abundance of clue cells in Gram-stained vaginal smears can also be used as a means to diagnose BV (Nugent et al., *J. Clin. Microbiol.* 29:297-301 (1991)).

Curiously, up to 50% of women diagnosed with BV may not exhibit all or any of the classic symptoms (Sweet, *Infect. Dis. Obstet. Gynecol.* 8:184-190 (2000); Schmid, *Int. J. Gynaecol. Obstet.* 67 Suppl. 1:S17-S20 (1999); Schwebke, *Int. J. Gynaecol. Obstet.* 67 Suppl. 1:S21-S23 (1999)). Such asymptomatic women are diagnosed as having BV due to the absence of numerically abundant populations with cellular morphologies that resemble those of lactobacilli. The equating of absence of lactobacilli with the occurrence of BV, has gained wide acceptance despite the fact that numerous studies have shown that a significant fraction of women without BV symptoms lack appreciable numbers of lactobacilli. This conundrum has not been resolved, nor is it recognized by the Centers for Disease Control. For example, the CDC publication, *Sexually Transmitted Diseases Treatment Guidelines* 2002 states the following: "BV is a clinical syndrome resulting from replacement of the normal hydrogen peroxide producing *Lactobacillus* sp. in the vagina with high concentrations of anaerobic bacteria (e.g., *Prevotella* sp. and *Mobiluncus* sp.), *G. vaginalis,* and *Mycoplasma hominis.*" This guidance equates the absence of lactobacilli with the existence of BV, and asserts that even women without vaginal lactobacilli, without overt classical symptoms, have BV.

The pH of the vagina is thought to be a principle factor in governing the composition of the vaginal microbial community in reproductive age women. A low pH environment selects for various acid-tolerant bacterial populations that can colonize and reproduce under such conditions, while precluding those that cannot (Pybus & Onderdonk *Microbes Infect.* 1:285-292 (1999)). Shifts in the structure of the vaginal microbial community that result in replacement of lactobacilli as the numerically dominant species, regardless of the cause, are typically accompanied by an upward swing in the environmental pH. This in turn provides an opportunity for abnormal flora such as yeasts and various anaerobes and bacterial species associated with BV to proliferate. It seems that the production of lactic acid per se is important, but the particular species of *Lactobacillus* present is less so since it varies among women. It also has been postulated that the production of hydrogen peroxide also may be an important mechanism by which some species of *Lactobacillus* suppress the growth of bacterial species that might otherwise represent a health threat. For example, Eschenbach et al., (*J. Clin. Microbiol.* 27:251-256 (1989)) have reported that vaginal lactobacilli that produce hydrogen peroxide are present in 96% of healthy women, but they are found in only 6% of women with BV. Importantly, decreased numbers of lactobacilli are correlated with an increased risk of acquiring HIV and STDs (Cohen et al., *AIDS* 9:1093-1097 (1995); Sewankambo et al., *Lancet* 350:546-550 (1997); Taha et al., *AIDS* 12:1699-1706 (1998); Taha et al. *J. Acquir Immune Defic. Syndr. Hum. Retrovirol.* 20:52-59 (1999); Royce et al., *J. Acquir. Immune Defic. Syndr. Hum. Retrovirol.* 20:382-386 (1999); Martin et al., *J. Infect. Dis.* 178:1053-1059 (1998);

Martin et al., *J. Infect. Dis.* 180:1863-1868 (1999)), and those that produce hydrogen peroxide have been shown to inactivate the HIV virus (Kiebanoff & Coombs, *J. Exp. Med.* 174: 289-292 (1991), which might lower the risk of HIV acquisition. The possible role of hydrogen peroxide in preventing colonization of the vagina by pathogenic bacteria is appealing since hydrogen peroxide is known to be microbicidal. However, direct evidence for the excretion of hydrogen peroxide in vivo is lacking, and the apparent failure of hydrogen peroxide to similarly affect members of the vaginal microbiota is a paradox that has not been resolved.

Many investigators have studied the species composition of vaginal flora and paid heed to the species of *Lactobacillus* present. It is widely believed that the principal *Lactobacillus* species in the vagina of healthy women are *Lactobacillus crispatus, Lactobacillus jensenii,* and *Lactobacillus gasseri* (Antonio et al., *J. Infect. Dis.* 180:1950-1956 (1999); Pavlova et al., *J. Appl. Microbiol.* 92:451-459 (2002)). There is, however, disagreement in the literature and various other species have been reported as members of normal vaginal flora. For example, Reid et al. (*FEMS. Immunol. Med. Microbiol.* 15:23-26 (1996)) sampled 100 healthy premenopausal women and cultivated the dominant aerobic or microaerophilic isolates of *Lactobacillus* from vaginal swab samples. Eight species were detected, the most common species being *L. jensenii*. The uncertainty regarding the actual species of *Lactobacillus* in the human vagina can in part be attributed to the difficulties of classifying lactobacilli on the basis of phenotypic criteria and the historical confusion surrounding the taxonomy of *Lactobacillus*. While investigators have focused attention on the role and importance of lactobacilli as members of the vaginal flora, the fact that between 10 and 42% of women lack appreciable numbers of lactobacilli (Eschenbach et al., *Clin. Infect. Dis.* 30:901-907 (2000); Hillier, *AIDS Res. Hum. Retroviruses* 14 Suppl 1: S17-S21 (1998); Larsen Monif, *Clin. Infect. Dis.* 32:e69-e77 (2001); Marrazzo et al., *J. Infect. Dis.* 185:1307-1313 (2002); Redondo-Lopez et al., *Rev. Infect. Dis.* 12:856-872 (1990)) has been nearly overlooked.

Prior efforts to characterize the vaginal flora have largely employed methods that are commonly used in clinical microbiology laboratories (Redondo-Lopez et al., *Rev. Infect. Dis.* 12:856-872 (1990), and references therein). These methods are inherently limited because they require cultivation of organisms on selective and nonselective media in the laboratory, after which they are classified into broad taxonomic groups based on phenotypic characters and microscopy. Slow growing, strictly anaerobic, or fastidious organisms may not be recovered by these methods. Others may have failed to grow because investigators are unaware of their inability to grow on selective media. Finally, the coarse classification methods used do not distinguish ecotypically distinct populations in samples. Traditional culture-dependent methods are tedious and labor intensive, and their use for the analysis of large numbers of samples is costly, permitting analysis of only small numbers of samples per study.

Recently, inventories of resident human bacterial flora done using cultivation-independent approaches based on analyses of 16S rRNA gene sequences have revealed a large degree of previously uncharacterized diversity even within well-studied and familiar microbial environments such as the human gingival crevice (Kroes et al., *Microbiol.* 96:14547-14552 (1999); Paster et al., *J. Bacteriol.* 183:3770-3783 (2001)), intestines (Favier et al., *App. Environ. Microbiol.* 68:219-226 (2002); Zoetendal et al., *J. Nutr.* 134:465-472 (2004)), inner ear (Frank et al., *J. Clin. Microbiol.* 41:295-303 (2003)), tongue (Kazor et al., *J. Clin. Microbiol.* 41:558-563 (2003)), and the esophagus (Pei et al., *Proc. Natl. Acad. Sci. USA* 101:4250-4255 (2004)).

SUMMARY OF THE DISCLOSURE

The present disclosure provides embodiments of a method for characterizing microbial populations. Exemplified by methods for characterizing microbiota in vaginal samples, the methods provided herein are widely applicable to the characterization of microbial communities. Also provided are probiotic regimens and methods for selecting appropriate probiotic regimens based on the normal vaginal microbiota of a subject. Reagents and kits for detecting normal vaginal microbiota and diagnosing pathogenic microorganisms in the vagina are also provided.

The foregoing and other objects, features, and advantages of the invention will become more apparent from the following detailed description, which proceeds with reference to the accompanying figures.

BRIEF DESCRIPTION OF THE SEQUENCE LISTING

Figure 1:
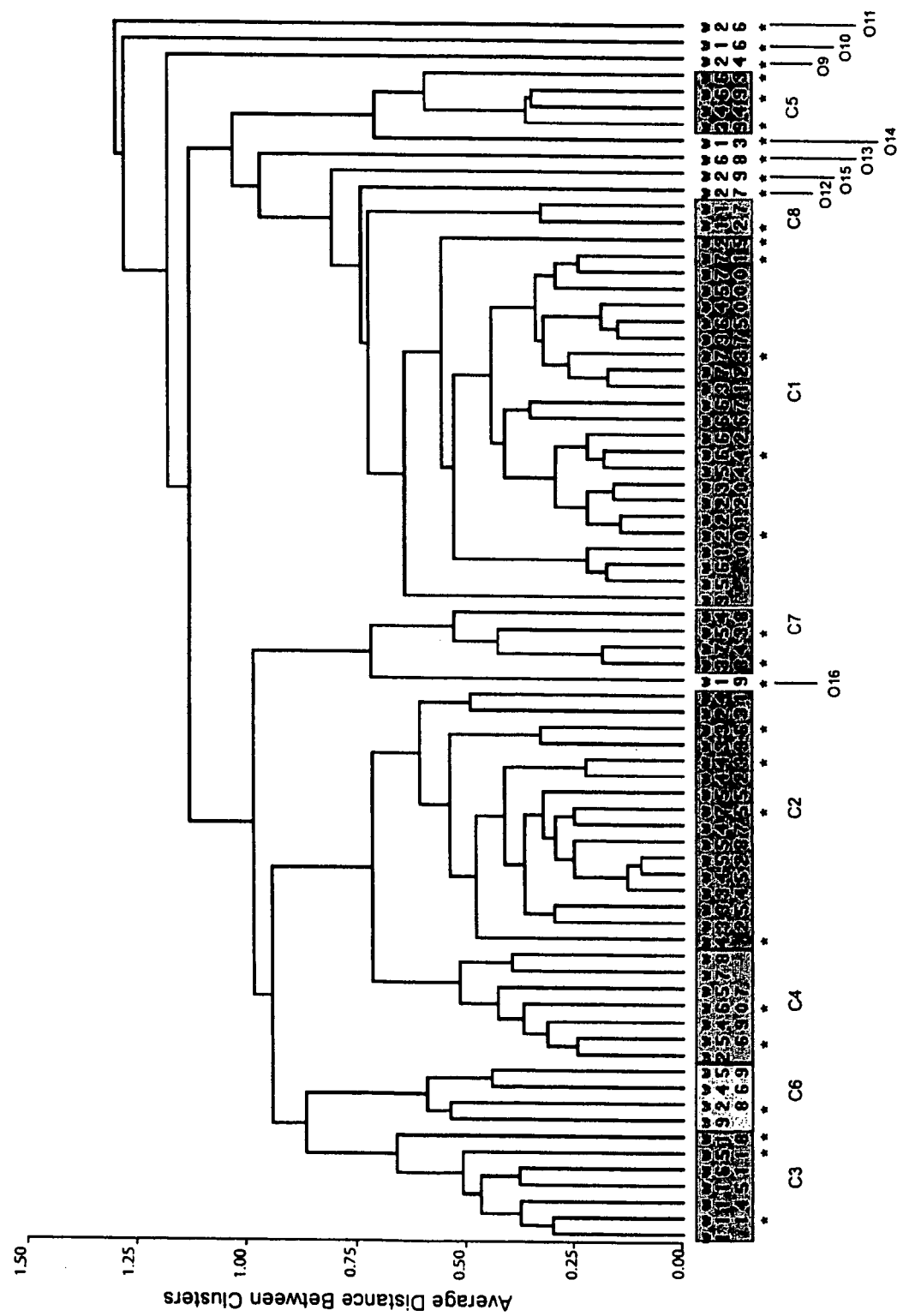
FIG. 1 is a dendrogram illustrating the relationships between normal categories of vaginal microbiota in Caucasian women.

SEQ ID NOs:1-5 are oligonucleotide primers for amplifying the 16S rRNA gene.

SEQ ID NOs:6-23 are oligonucleotides that specifically hybridize and/or specifically amplify specified species of microorganisms.

DETAILED DESCRIPTION

I. Summary of Specific Embodiments

The present disclosure provides a method for assessing the phylogeny of populations in microbial communities. In an embodiment, the present disclosure provides a method of identifying one or more microbial communities involving providing a plurality of microbial profiles obtained from samples of microorganisms; identifying one or more consensus profiles from among the plurality of microbial profiles; and, assigning at least a subset of the plurality of microbial profiles to a consensus profile that defines a microbial community. The microbial profiles can be obtained by analysis of a variety of sample sources, including environmental samples, plant samples, animal subjects and human subjects. The samples can include symbiotic microorganisms, commensal microorganisms, pathogenic microorganisms, environmental microorganisms, and mixtures thereof in any combination.

Typically, the microbial profiles are provided by a culture-independent method. For example, the microbial profiles can be provided by preparing a nucleic acid sample including at least one molecular indicator of identity from at least one species of microorganism present in the sample of microorganisms. The molecular indicator of identity is then detected to provide a microbial profile. Typically, the molecular indicator of identity is polymorphic polynucleotide, such as a phylogenetically informative gene. One example of a molecular indicator of identity is an rRNA gene, for example the 16S rRNA gene. The molecular indicator of identity can be detected, for example, by determining the nucleotide sequence ("sequencing") the polymorphic polynucleotide, or a portion or subsequence thereof. In an embodiment, the molecular indicator of identity is detected by evaluating the sizes of terminal restriction fragments of the 16S rRNA gene. For example, the terminal restriction fragments of the 16S rRNA gene can be evaluated by T-RFLP (terminal restriction fragment length polymorphism) analysis.

In an embodiment, related profiles (that is, one or more consensus profiles) are identified using a clustering alogorithm. A clustering algorithm is typically a statistical method, such as a cubical clustering criterion analysis, a pseudo F analysis or a pseudo $T^2$ test, or a combination thereof.

Throughout this disclosure the method is exemplified by the characterization of bacterial populations in the human vagina. In this exemplary embodiment, the microbial community is a community of normal vaginal microbiota. In such an embodiment, a plurality of vaginal microbiota profiles are obtained from women without a vaginal pathology ("normal" women); one or more consensus profiles is identified among the plurality of vaginal microbiota profiles; and, at least a subset of the plurality of vaginal microbiota profiles is assigned to a consensus profile that defines a normal vaginal microbiota.

In an embodiment, the disclosure provides a method for categorizing a vaginal microbiota community as normal. Such a method involves identifying one or more predominant species of microbiota in a vaginal sample, thereby producing a vaginal microbiota profile; and, categorizing the vaginal microbiota population as normal by assigning the vaginal microbiota profile to a category of normal vaginal microbiota. Most commonly, the predominant species of microbiota is a species of bacteria, or a combination of species of bacteria. Nonetheless, the predominant species of microbiota can also include species of yeast, species of fungi and species of viruses.

In certain embodiments, the predominant species of microbiota is a species of bacteria selected from among *Lactobacillus crispatus, Lactobacillus iners, Lactobacillus jensenii, Lactobacillus gasseri, Lactobacillus coleohominis, Staphylococcus* sp., *Streptococcus* sp.; *Atopobium vaginae, Lachnospiraceae* sp., *Megasphaera* sp., *Enterococcus faecalis, Peptoniphilus* sp., *Anaerococcus* sp., *Micromonas* sp., *Gemella palaticanis, Dialister* sp., *Clostridaceae* sp. e.g., *Clostridium perfringens, Aerococcus* sp., *Veillonella* sp., *Finegoldia magna, Granulicatella elegans, Gardinerella vaginalis, Pseudomonas* sp., *Mycoplasma* sp., *Mobiluncus muleiri, Peptostreptococcus anaerobis, Escherichia coli, Shigella* sp., or a bacterium of the order Clostridiales.

Normal vaginal microbiota is shown herein to vary among women, and varies statistically between women of different racial and/or ethnic backgrounds. Accordingly, embodiments of the method described herein can be used to determine the categories of normal (and conversely, the categories of abnormal) vaginal microbiota in groups of women regardless of how the groups are defined, that is regardless of how the distinctions between groups of women are drawn. For example, the normal vaginal microbiota can be determined in women of different racial and/or ethnic ancestry, and among women from different geographic locations. In an embodiment, the categories provided include categories of normal vaginal microbiota prevalent among Caucasian women, for example, women of European ancestry. In other embodiments, the categories of normal vaginal microbiota are commonly found among women of African ancestry, among women of Asian ancestry, etc. Thus, embodiments disclosed herein are applicable regardless of the racial and/or ethnic classification of the subjects, and can be used to determine the categories of normal vaginal microbiota in any group of women.

For example, among Caucasian women, seven categories of normal vaginal microbiota predominate: I) *Lactobacillus iners*; II) *Lactobacillus crispatus*; III) *Lactobacillus crispatus* and *Lactobacillus jensenii*; IV) *Lactobacillus iners, Lactobacillus crispatus*, and *Lactobacillus gasseri*; V) *Atopobium vaginae*, and one or more species of the order Clostridiales; VI) *Lactobacillus crispatus* and *Lactobacillus gasseri*; and VII) *Lactobacillus crispatus, Lactobacillus iners*, and *Lactobacillus jensenii*. Additionally, individuals with vaginal microbiota predominated by *Streptococcus* sp., *Veillonella* sp., and *Gemella palaticanis*; *Streptococcus* sp., or *Lactobacillus gasseri* are observed.

An overlapping set of bacterial phylotypes are found in normal women of African ancestry, with five categories predominating: I) *Lactobacillus iners*; II) *Lactobacillus crispatus*; V) *Atopobium vaginae*, and one or more species of the order Clostridiales; VIII) *Lactobacillus gasseri*; and IX) *Megasphaera* sp., and one or more species of the order Clostridiales. Additional microbial profiles include *Lactobacillus gasseri, Gardinerella vaginalis* and *Streptococcus* sp.; *Escherichia coli* and *Shigella* sp.; *Lactobacillus jensenii* and *Streptococcus* sp.; and, *Gemella palaticanis* and *Mycoplasma* sp. These species include: *Peptoniphilus* sp., *Anaerococcus tetradius, Micromonas* sp., *Dialister* sp., *Aerococcus* sp., *Veillonella* sp., *Finegoldia magna, Granulicatella elegans, Clostridium perfringens, Mobiluuncus mulieri, Peptostreptococcus anaerobius, Pseudomonsa* sp., uncultured *Mycoplasma* sp (GENBANK® Accession No. S000123722), uncultured bacterium (GENBANK® Accession No. S000329832) and additional uncultured species represented by GENBANK® Accession Nos. S000126539, S00343908, S000343909, S000343911, S000245992, and a species previously not identified in vaginal samples represented by GENBANK® Accession Nos. S000350386.

As described above, the predominant species of microbiota are typically identified using a culture-independent method of identification. For example, one or more predominant species of microbiota can be identified using PCR with selective primers, quantitative PCR with selective primers, DNA-DNA hybridization, RNA-DNA hybridization, in situ hybridization, any of a variety of comparable techniques, and combinations thereof. Optionally, DNA-DNA hybridization and/or RNA-DNA hybridization is performed on a microarray. In another embodiment, one or more predominant species of microbiota can be identified by determining the nucleotide sequence of a portion of a microbial genome, such as a 16S rRNA gene.

In another embodiment, a method for identifying at least one predominant species of microbiota in a vaginal sample is disclosed. Such a method for identifying predominant species of microbiota in a vaginal sample involves providing a vaginal sample comprising one or more species of vaginal microbiota, and detecting at least one predominant species of microbiota in the vaginal sample by a culture-independent method. One embodiment of the method involves preparing a nucleic acid sample including a molecular indicator of identity from at least one species of microbiota present in the vaginal sample and detecting the molecular indicator of identity. For example, the method can involve preparing at least one nucleic acid sample by preparing a DNA sample. As indicated above, the molecular indicator of identity can be a polymorphic polynucleotide, such as an rRNA gene (for example, a 16S rRNA gene). The molecular indicator of identity can be detected by determining the nucleotide sequence of the polymorphic polynucleotide, such as the 16S rRNA gene, or a portion or subsequence thereof. Alternative embodiments for detecting the molecular indicator of identity also include PCR with selective primers, quantitative PCR with selective primers, DNA-DNA hybridization, RNA-DNA hybridization, in situ hybridization, and combinations thereof. For example, the polymorphic polynucleotide can be detected by hybridization to a species specific probe. In such an example, the species specific probe hybridizes to a polymorphic target nucleic acid, such as a 16S rRNA gene. Optionally, the nucleic acid can be hybridized to at least one array comprising a plurality of species specific probes, e.g., a plurality of species specific probes, each of which identifies a species of vaginal microbiota. Detecting the molecular indicator of identity can also be accomplished using protein probes (such as antibodies) that bind to polymorphic target proteins, for example polymorphic target proteins that identify the species of vaginal microbiota.

In another embodiment, the disclosure relates to methods for establishing or maintaining a normal bacterial community. These methods involve identifying one or more predominant species of microbiota in a biological sample to produce a microbiota profile; assigning the microbiota profile to a category of normal microbiota; and providing a composition comprising one or more species of microorganism selected from the microbiota profile. In certain embodiments, the methods involve identifying and categorizing microbiota in a subject. Typically, the identification is accomplished using culture-independent methods. For example, as disclosed herein, the predominant species can be identified by PCR using selective primers, quantitative PCR with selective primers, DNA-DNA hybridization, RNA-DNA hybridization and/or in situ hybridization. In some cases the hybridization is performed on a microarray. Alternatively, the one or more predominant species can be identified by determining the nucleotide sequence of a portion of a microbial genome, such as a 16S rRNA gene.

For example, in some embodiments, the methods involve identifying normal microbiota from a vaginal sample from a subject in order to select a safe and effective probiotic regimen for establishing or maintaining a normal category of vaginal microbiota, such as a normal vaginal microbiota that is not dominated by *Lactobacillus* sp. Embodiments of the method for selecting a safe and effective probiotic regimen involve producing a vaginal microbiota profile by identifying one or more predominant species of microbiota in a vaginal sample; assigning the vaginal microbiota profile to a category of normal vaginal microbiota; and, selecting a safe and effective probiotic regimen comprising one or more species of microbiota selected from the vaginal microbiota profile.

In certain embodiments, the predominant species of bacteria is/are one or more of: *Lactobacillus crispatus, Lactobacillus iners, Lactobacillus jensenii, Lactobacillus gasseri, Lactobacillus coleohominis, Staphylococcus* sp., *Streptococcus* sp., *Atopobium vaginae*, Lachnospiraceae sp., *Megasphaera* sp., *Enterococcus faecalis, Peptoniphilus* sp., *Anaerococcus* sp., *Micromonas* sp., *Gemella palaticanis, Dialister* sp., *Aerococcus* sp., *Veillonella* sp., *Finegoldia magna, Granulicatella elegans, Gardinerella vaginalis, Pseudomonas* sp., *Mycoplasma* sp., *Mobiluncus muleiri, Peptostreptococcus anaerobis, Escherichia coli, Shigella* sp., or a bacterium of the order Clostridiales. For example, in one embodiment, the category of normal vaginal microbiota is characterized by one or more predominant species of bacteria selected from the following categories: a) *Lactobacillus iners*; b) *Lactobacillus crispatus*; c) *Lactobacillus crispatus* and *Lactobacillus jensenii*; d) *Lactobacillus iners, Lactobacillus crispatus* and *Lactobacillus gasseri*; e) *Atopobium vaginae* and one or more species of the order Clostridiales; f) *Lactobacillus crispatus* and *Lactobacillus gasseri*; g) *Lactobacillus crispatus, Lactobacillus iners* and *Lactobacillus jensenii*; h) *Streptococcus* sp., *Veillonella* sp. and *Gemella palaticanis*; i) *Streptococcus* sp.; and j) *Lactobacillus gasseri*. These are categories common among Caucasian women. In another embodiment, the category of normal vaginal microbiota is characterized by one or more predominant species of bacteria selected from the following categories: a) *Lactobacillus iners*; b) *Lactobacillus crispatus*; c) *Atopobium vaginae* and one or more species of the order Clostridiales; d) *Lactobacillus gasseri*; e) *Megasphaera* sp. and one or more species of the order Clostridiales; f) *Lactobacillus gasseri, Gardinerella vaginalis* and *Streptococcus* sp.; g) *Escherichia coli* and *Shigella* sp.; h) *Lactobacillus jensenii* and *Streptococcus* sp.; and, i) *Gemella palaticanis* and *Mycoplasma* sp. These categories are common among women of African ancestry.

In other embodiments, probiotic regimens for establishing or maintaining normal categories of vaginal microbiota are disclosed herein. For example, probiotic regimens including at least one composition that promotes growth of one or more species of microorganisms selected from a normal vaginal microbiota are disclosed. Such a composition can include one or more pharmaceutical and/or nutritional composition that promotes growth of one or more species of microorganisms selected from a normal vaginal microbiota and/or the composition can include one or more species of microorganisms selected from a normal vaginal microbiota, or combinations thereof. For example, probiotic regimens including a species other than a species of *Lactobacillus*, such as *Atopobium vaginae* are described. In some cases, the probiotic regimen also includes one or more species selected from *Lactobacillus crispatus, Lactobacillus iners, Lactobacillus jensenii, Lactobacillus gasseri, Lactobacillus coleohominis, Staphylococcus* sp., *Streptococcus* sp., *Atopobium vaginae*, Lachnospiraceae sp., *Megasphaera* sp., *Enterococcus faecalis, Peptoniphilus* sp., *Anaerococcus* sp., *Micromonas* sp., *Gemella palaticanis, Dialister* sp., *Aerococcus* sp., *Veillonella* sp., *Finegoldia magna, Granulicatella elegans, Gardinerella vaginalis, Pseudomonas* sp., *Mycoplasma* sp., *Mobiluncus muleiri, Peptostreptococcus anaerobis, Escherichia coli, Shigella* sp., and a bacterium of the order Clostridiales.

Methods of formulating probiotic regimens based on selecting one or more species of microorganism suitable for establishing or maintaining normal vaginal microbiota in a human or animal subject are also provided. The methods for formulating probiotic regimens involve identifying one or more predominant species of microbiota in a vaginal sample to produce a vaginal microbiota profile; assigning the vaginal microbiota profile to a category of normal vaginal microbiota; and providing a pharmaceutically acceptable formulation comprising one or more species of microorganism selected from the microorganisms of a category of normal vaginal microbiota, such as the categories listed above.

Typically, the microorganism is selected from among the microorganisms characteristic in of a category of normal vaginal microbiota, such as a category of normal vaginal microbiota selected from among the normal categories of vaginal microbiota observed in a definable population to which the subject belongs. For example the category of normal vaginal microbiota can be a category of normal vaginal microbiota selected from among the categories of normal vaginal microbiota found in a racially or ethnically defined population of women. Alternatively, the category can be selected from among those of a population of female human or animal subjects defined by one or more personal or environmental, e.g., geographic, characteristics other than race or ethnicity.

In certain examples, the method for formulating a probiotic regimen involves providing a pharmaceutically acceptable formulation comprising one or more species of microorganism from a category of normal vaginal microbiota selected from the group consisting of:
a) *Lactobacillus iners;*
b) *Lactobacillus crispatus;*
c) *Lactobacillus crispatus* and *Lactobacillus jensenii;*
d) *Lactobacillus iners, Lactobacillus crispatus,* and *Lactobacillus gasseri;*
e) *Atopobium vaginae* and one or more species of the order Clostridiales;
f) *Lactobacillus crispatus* and *Lactobacillus gasseri;*
g) *Lactobacillus crispatus, Lactobacillus iners* and *Lactobacillus jensenii.*
h) *Streptococcus* sp., *Veillonella* sp. and *Gemella palaticanis;*
i) *Streptococcus* sp.; and
j) *Lactobacillus gasseri.*

In another example the method of formulating a probiotic regimen involves providing a pharmaceutically acceptable formulation comprising one or more species of microorganism from a category of normal vaginal microbiota selected from the group consisting of:
a) *Lactobacillus iners;*
b) *Lactobacillus crispatus;*
c) *Atopobium vaginae* and one or more species of the order Clostridiales;
d) *Lactobacillus gasseri;*
e) *Megasphaera* sp. and one or more species of the order Clostridiales;
f) *Lactobacillus gasseri, Gardinerella vaginalis,* and *Streptococcus sp.;*
g) *Escherichia coli* and *Shigella sp.;*
h) *Lactobacillus jensenii* and *Streptococcus sp.;* and,
i) *Gemella palaticanis* and *Mycoplasma* sp.

In another embodiment, the disclosure provides methods for expressing a product encoded by a recombinant nucleic acid, such as a recombinant protein in the vagina of a subject. Such methods involve selecting an appropriate host strain of microorganism based on the vaginal microbiota that is normal for the subject. A recombinant nucleic acid encoding the product, e.g., protein or RNA, of interest is introduced (e.g., transformed) into the host microorganism, which is then introduced into the vagina of a subject. The host strain is able to stably colonize the vagina of the subject and express the recombinant product (such as a recombinant polypeptide or an RNA, e.g., an siRNA or a ribozyme).

Also described are kits including a plurality of species specific probes suitable for detecting microorganisms from a vaginal sample of microorganisms. For example, the kit can include a plurality of species specific probes and/or primers, each of which identifies a particular species (or group of species, such as a genus or phylum) of normal vaginal microbiota. The probes can be nucleic acid probes, such as DNA or RNA polynucleotides or oligonucleotides that specifically hybridize and/or specifically amplify a particular species or group of microorganisms. Alternatively, the probes can be binding proteins, such as antibodies, receptors, ligands or receptor or ligand analogues, that interact with a protein or other antigen produced by the microorganism.

In an embodiment, the kit includes a plurality of probes and/or primers that detect species selected from the group consisting of *Lactobacillus crispatus, Lactobacillus iners, Lactobacillus jensenii, Lactobacillus gasseri, Lactobacillus coleohominis, Staphylococcus* sp., *Streptococcus* sp., *Atopobium vaginae,* Lachnospiraceae sp., *Megasphaera* sp., *Enterococcus faecalis, Peptoniphilus* sp., *Anaerococcus* sp., *Micromonas* sp., *Gemella palaticanis, Dialister* sp., *Aerococcus* sp., *Veillonella* sp., *Finegoldia magna, Granulicatella elegans, Gardinerella vaginalis, Pseudomonas* sp., *Mycoplasma* sp., *Mobiluncus muleiri, Peptostreptococcus anaerobis, Escherichia coli, Shigella* sp., and/or a bacterium of the order Clostridiales. In one example, the kit includes a plurality of probes selected from SEQ ID NOs:6-23. For example, the kit can include one or more species specific probes selected from SEQ ID NOs:6-23 and one or more universal primers, e.g., SEQ ID NO:1 and SEQ ID NO:3. Optionally, the kit can include probes (and/or primers) for one or more species of pathogenic microorganism in addition to the probes (and/or primers) for the species of normal vaginal microbiota.

In some embodiments, the plurality of probes are arrayed on a solid matrix, such as a slide, a chip, a pin, a bead or a membrane. In an embodiment, the solid matrix is a test strip, or dipstick, or a lateral flow device.

II. Terms

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press (1994)(ISBN 0-19-854287-9); Kendrew et al., (eds.), *The Encyclopedia of Molecular Biology*, published by Blackwell Science Ltd. (1994)(ISBN 0-632-02182-9); and Robert A. Meyers (ed.), *Molecular Biology and Biotechnology: a Comprehensive Desk Reference*, published by VCH Publishers, Inc. (1995) (ISBN 1-56081-569-8).

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In order to facilitate review of the various embodiments of this disclosure, the following explanations of specific terms are provided:

The term "microbe" refers to an organism that is too small to be visible with the naked eye, and is used synonymously with the term "microorganism." Microorganisms include bacteria (Archaea, Eubacteria), yeast, fungi, and for the purposes of this disclosure, shall be understood to include viruses. The term "species of microorganism" is used herein to refer to a taxonomically and/or genetically distinct group of microorganism. The term "predominant species" (for example, predominant species of microorganism) refers to one or more species that is/are numerically more frequent than other species in a mixed sample or population. For example, a predominant species may be the most numerically frequent species in a mixed sample or population, or a predominant species may be one of several numerically frequent species present in a mixed sample or population. In an embodiment, a predominant species is at least 10% of the mixed sample or population. For example, a predominant species can be at least 20%, or at least 30%, frequently greater than about 40%, or greater than 50% of the mixed population. In some cases, the predominant species is often than about 60%, sometimes greater than about 70%, and can be greater than 80% or even 90% of the mixed sample or population. In another embodiment, a predominant species is at least 2× as prevalent in the mixed sample as another species of microorganism. Alternatively, the predominant species is at least 3× as frequent in the mixed sample as other organisms. In some cases, the predominant species is at least 4×, or at least about 5×, or even as much as 10× as frequent in the mixed sample or population than another species of microorganism.

The term "microbiota" refers to an assemblage of microorganism localized to a distinct environment. For example, "vaginal microbiota" are an assemblage of one or more species of microorganisms that are localized to, or found in, a vagina. "Normal vaginal microbiota" are a population of microorganisms that localize to the vagina in a normal, that is, a non-pathological or non-pathogenic, state. For example, a sample of normal vaginal microbiota is obtained from a woman without a vaginal pathology, that is, from a woman with no sign or symptom corresponding to or resulting from a pathology of the vagina. Normal vaginal microbiota can be obtained from a woman with a pathology of an organ or tissue other than the vagina. In a medical context, the term "microflora" is often used synonymously with the term "microbiota."

The term "microbial community" refers to one or more microbial populations found together in a shared environment. For example, a shared environment can be a defined site or location on or in a subject (e.g., a host), or can be an environmental site or location not associated with a subject. Thus, a shared environment can be a specific organ or tissue within the body of a subject, such as the skin, the oral cavity, the gingival crevice, the esophagus, the ear, the small intestine, the large intestine, the rectum, the vagina, etc. Alternatively, a shared environment can be a site or location, such as soil, water, or another environmental source not pertaining to a particular subject (such as a human subject). For purposes of clarity, samples obtained from an environment on or in (pertaining to a) subject will be so designated, for example, a sample obtained from a human subject, a sample obtained from an animal subject, a sample obtained from a plant subject. In contrast, a sample obtained from a source other than a subject will be referred to as an "environmental sample."

Individual species of microorganisms obtained from a subject, such as a human, animal or plant subject, may exist in various relationships with respect to the subject (or host). For example, the microorganism can be a "symbiotic microorganism" that exists in a relationship with its host that provides a benefit to both the microorganism and the host, that is, a mutually beneficial relationship. The microorganism also can be a "commensal microorganism" that exists in a relationship that is beneficial to the microorganism and neither benefits nor harms the host. Alternatively, the microorganism can be a "parasitic microorganism" that derives benefit from its host at the expense of or detriment to the host. Additionally, a microorganism can be a "pathogenic microorganism" that causes or is capable of causing a disease state or condition in the host.

A "microbial profile" is a set of the species and/or strains of microorganisms present in a sample of microorganisms. To the extent that a sample of microorganisms is obtained from, and corresponds to the species found in, a shared environment, the microbial profile details the species present in a microbial community. The term "consensus profile" is used herein to refer to the species common to multiple samples with similar microbial profiles. That is, a consensus profile includes the species of microorganisms that are common to each of multiple samples, which may or may not have additional unshared species.

The term "molecular indicator of identity" refers to any molecule that differs between species or strains, and for which the difference can be detected. Most typically, a molecular indicator of identity is polymorphic nucleic acid, or a polymorphic polypeptide encoded by a polymorphic nucleic acid. The term "polymorphic" or "polymorphism" refers to a nucleic acid or polypeptide that exists in two or more variant forms. The variant forms may be detectable at the molecular level (e.g., at the nucleic acid or polypeptide level) or may be detectable as functional variants, for example, by phenotypic differences between species or strains. In some cases, a molecular indicator of identity is not directly encoded by a polymorphic polynucleotide. For example, polymorphic glycoproteins can be detected based on differences in their carbohydrate moieties. In addition, in some cases the molecular indicator of identity can be a metabolic product that differs between species, for example a detectable metabolite, such as a secondary metabolite, that differs between species.

A polymorphic nucleic acid can include a "phylogenetically informative gene," that is, a functional genetic element that differs between species. A phylogenetically informative gene is one in which the differences in nucleotide sequence reflect the evolutionary relationships of organisms. More generally, polymorphic nucleic acids are characterized by polymorphic polynucleotide sequences, that is, polynucleotide sequences with one or more nucleotide differences when aligned across a window of comparison. Such differences can be detected by determining the nucleotide sequence of the polymorphic polynucleotide, that is, by sequencing the polynucleotide, or at least a portion therof, using any known methods, including automated methods, for sequencing nucleic acids. Alternatively, a polymorphism in a nucleic acid can be detected by a variety of techniques including RFLP, AFLP, SSCP, SNP, etc.

An "rRNA gene" is one exemplary polymorphic nucleic acid. The rRNA genes encode the ribonucleic acid ("RNA") components of ribosomes, and can be categorized based on the size of the ribosomal component in which the encoded RNA is localized. Prokaryotic rRNA genes include: the 16S rRNA gene, the 23S rRNA gene and the 5S rRNA gene. Eukaryotic rRNA genes include the 18S, 28S and 5.8S rRNA genes, respectively.

A composition for administration to a subject (such as a probiotic regimen or formulation) should provide the desired benefit(s) without causing side effects (adverse events) that would outweigh those benefits. Accordingly, a pharmaceutical composition should be both safe and effective. The term "safe" is used to indicate that the incidence and severity of adverse events is acceptable in view of the desired benefits produced by administration of the composition. The fundamental basis of the quantitative relationships between exposure to an agent and the incidence of an adverse response is the dose-response assessment. Analysis of dose-response relationships start with the determination of the critical effects to be quantitatively evaluated. Approaches for characterizing threshold dose-response relationships include determining no observed adverse effect levels (NOAEL) or lowest observed adverse effect levels (LOAELs). An "adverse event" (AE) can be defined as any unfavorable and unintended sign including an abnormal laboratory finding, symptom or disease temporally associated with use of a medicinal (investigational) product whether or not related to the investigational product. An adverse drug reaction (ADR) means that a causal relationship between a medicinal (investigational) product and an adverse event is at least a reasonable possibility, that is, the relationship cannot be ruled out. The term "effective" indicates that the composition has the capacity or power to produce a desired effect. Efficacy has been defined as the maximum ability of a drug or treatment to produce a result regardless of dosage. The efficacy of the product should be determined based on an appropriately designed research and/or clinical study. In the procedure mandated by the FDA, Phase II clinical trials gauge efficacy, and Phase III trials confirm it.

III. Identification of Microbial Communities

The present disclosure provides methods for analyzing microbial communities that are applicable in a wide variety of settings to determine the constituent species of microbiota in an environment. The constituent species in a sample are identified, providing a microbial profile that distinguishes the predominant species of microorganisms in the sample. By ascertaining the microbial profile from numerous samples with a shared characteristic, consensus profiles can be determined that provide a reference point for further analysis.

Microbial profiles are obtained by identifying the predominant species present in samples of microorganisms. The sample of microorganisms can be obtained from essentially any environmental source. The source can be a particular tissue or organ on or in a host organism, or can be an external environmental source such as soil, water, waste effluent, etc. For example, microbial profiles can be ascertained to determine the diversity and community structure of bacterial populations in different ecosystems as disclosed in Liu et al., *Appl Env Microbiol* 63:4516-4522 (1997); Zhou et al., *Microbiology* 150:2565-2573 (2004), which are incorporated herein in their entirety for all purposes.

For example, samples of microorganisms can be obtained from an external surface of a subject organism by wiping, swabbing, scraping or other mechanical means for removing objects at or near the surface of an organism. Optionally, a wetting agent, buffer, lubricant or other agent can be employed to facilitate recovery of the sample. Samples can be similarly obtained from orifices and internal surfaces, such as the surface of a body cavity such as the oral cavity, the gingival crevice, the nose, the esophagus, the ear, the small intestine, the large intestine, the rectum, the vagina, etc.

Microbial communities are typically found on both external and internal surfaces of a subject organism, and can be sampled in both normal and disease conditions. Under certain conditions, typically pathological (or abnormal) conditions, samples of microorganisms can be obtained from inside the body of a subject, from a source that is not contiguous with the external environment. Such samples, typically must be obtained using more invasive procedures, including percutaneous blood sampling, sampling of cerebrospinal fluid, for example by lumbar puncture, and laparoscopically guided sampling of the peritoneneal cavity. Samples can be obtained from any subject for which the identification or classification of resident microbiota is desirable. Accordingly, subjects that serve as hosts for microbial communities can include, human and other animal subjects as well as plant subjects.

Once the sample is obtained, the constituent species are determined. To prevent introduction of bias into the analysis, the constituent species of a sample are determined using a method that does not require preliminary culturing of the microorganisms. Identification of the constituent species of microorganism, that is identification of the predominant species (optionally, the identification of all of the species) establishes a microbial profile for the sample. Depending on the source of the sample, and on the status of the subject, for example, the health or disease status of the organism, the samples can include one or more predominant species of microorganisms. The species identified can include symbiotic microorganisms, commensal microorganisms and/or pathogenic microorganism. For example, in a sample obtained from a subject without a sign or symptom of a disease (e.g., a "normal" subject), the predominant species are likely to be symbiotic and/or commensal microorganisms. In contrast, pathogenic microorganisms are more likely to be observed in a sample from a subject with a disease, condition, symptom or sign related to a pathological condition. Thus, the methods described herein can be used to determine the communities of microorganisms present in both normal and disease (abnormal) states.

IV. Culture-Independent Methods

Typically, the microbial profile is established by detecting at least one molecular indicator of identity from which the species of microorganism can be determined.

Several culture-independent approaches are useful for analyzing large numbers of samples and offer the possibility of being able to detect statistically significant differences between normal communities and those associated with diseases. Culture-independent methods offer significant advantages over methods for classifying microorganisms that require culture prior to analysis. For example, culture-independent methods decrease labor and materials costs by eliminating the requirement that colonies of microorganisms be established prior to analysis. Similarly, culture-independent methods increase the throughput so that it is feasible to analyze larger numbers of samples making it possible to determine statistically relevant differences between categories. Most importantly, by eliminating the need for culturing of microorganisms prior to analysis, bias due to preferential growth under various culture conditions is eliminated. By eliminating this bias, it becomes possible to comprehensively determine the variety of microbiota that inhabit an environment under normal and perturbed conditions.

Culture-independent methods for identifying the constituent species in a sample of microorganisms involve detecting one or more molecular indicators of identity. A molecular indicator of identity can be any molecular species present in or produced by the microorganism, so long as it can be detected directly or indirectly. Preferably, the molecular species exists in sufficiently polymorphic forms that it can alone, or in combination with other molecular species, be used to determine the identity of the microorganism from which it is obtained. A molecular indicator of identity can be a protein species that differs in a predictable way between species. For example, the molecular indicator of identity can be an antigen that differs between species of microorganism and can be distinguished, e.g., by the binding of an antibody.

More typically, the culture-independent methods involve preparing a nucleic acid sample from a sample of microorganisms, and detecting at least one molecular indicator of identity that can be used to determine the identity of the constituents of the sample. The nucleic acid can be either DNA, RNA, or both, and can be prepared by any methods known in the art for the isolation and purification of nucleic acids. Exemplary procedures sufficient to guide one of ordinary skill in the preparation of nucleic acid samples from microorganisms can be found, for example, in Kowalchuk et al. (Eds.) *Molecular Microbial Ecology Manual*, $2^{nd}$ Edition, Kluwer Academic Publishers (2004); Sambrook et al. (ed.), *Molecular Cloning: A Laboratory Manual*, $2^{nd}$ ed., vol. 1-3, Cold Spring Harbor Laboratory Press, Cold Spring Harbor, N.Y. (1989); and Ausubel et al., *Short Protocols in Molecular Biology*, $4^{th}$ ed., John Wiley & Sons, Inc. (1999)). Following preparation of a nucleic acid sample from the sample of microorganisms, one or more molecular indicators of identity are detected to determine the constituent species in the sample.

Usually, the nucleic acid is a polymorphic polynucleotide sequence. The molecular indicator of identity can be a phylogenetically informative gene. Phylogenetically informative genes include functional genomic sequences, such as, protein coding regions and/or regulatory regions. Phylogenetically informative genes (e.g., homologs or orthologs of a gene) differ between species but originate from a common ancestor. The polynucleotide sequences of orthologous genes in different species have diverged over time accumulating mutations, that is, nucleotide alterations (which can be insertions, deletions, point mutations, and/or recombination events), which can be detected using any of a variety of methods for detecting sequence differences. Typically, a phylogenetically informative gene is one for which at least one ortholog can be detected among a large number of species of microorganisms.

In one culture-independent method, profiles of microbial communities based on the terminal restriction fragments ("T-RFs") of 16S rRNA genes are produced. The 16S rRNA gene is particularly suitable as a molecular indicator of identity for the identification and phylogenetic analysis of microorganisms. The 16S rRNA gene offers several significant advantages as a molecular indicator of identity. For example, the 16S rRNA gene is highly conserved and universal PCR primer sets exist that can amplify the 16S rRNA gene from the overwhelming majority of bacteria and Archea, respectively. The 16S rRNA gene also includes regions that are less well conserved making it possible to design probes specific for the various taxons. Additionally, the 16S rRNA gene is believed to have changed at a fairly constant rate during evolution, making it, in effect, an evolutionary clock with each nucleotide difference translating to an evolutionary time unit.

The approximately 1500 bp sequence of the 16S rRNA gene contains enough information to predict the identity and phylogeny of an organism with high precision. Furthermore, an extensive, rapidly growing database exists for this gene. For example, the ARB database (available on the world wide web at arb-home.de) contains over 25,000 aligned 16S rRNA gene sequences. Additional databases include that of the Ribosomal Database Project (Cole et al., *Nuc. Acids. Res.* 31:442-443 (2003) and the NCBI database (available on the world wide web at ncbi.nlm.nih.gov/entrez).

T-RF profiles provide insight to the phylogeny of the populations present in the samples. Briefly, rRNA genes are amplified from total community DNA in a polymerase chain reaction ("PCR") with one or both amplification primers labeled with a detectable moiety, such as a fluorescent dye. The mixture of resulting rRNA amplicons is then digested with one or more restriction enzymes, and the sizes and relative abundances of the fluorescently labeled T-RFs are determined using an automated DNA sequencer. Since differences in the sizes of T-RFs reflect differences in the sequences of 16S rRNA genes (sequence polymorphisms), phylogenetically distinct populations of organisms can be resolved. Thus, the pattern of T-RFs is a composite of DNA fragments with distinct lengths that reflects the diversity and composition of the predominant populations in the community. This method, referred to as T-RFLP, provides a useful method for assessing microbial community structure, for example under various environmental conditions (e.g., based on lack or presence of a disease state in the host), or over temporal or spatial parameters based on the gain or loss of specific fragments from the profiles. Optionally, T-RF analysis can be coupled to 16S rRNA clone library construction and clone sequencing.

Additional examples of phylogenetically informative genes suitable as molecular indicators of identity include: rpoB; gyrB; gyrA; tmRNA; recA; EF-Tu (tuf); groEL (cnp60, hsp60); atpD; ompA gene; gapA; pgi;fusA; ileS; lepA; leuS; pyrG; recG; rplB. Other genes (for example functional genes encoding related enzymes that perform a defined function) also can be utilized, at least with respect to narrower groups of microorganisms. Examples of such functional genes include the pmoA/amoA genes; the mmoX gene; the nifH gene; the nirS gene; the nirK gene; the norB gene; the mcrA gene; and the rbcL gene. Of course, one of ordinary skill will appreciate that any polymorphic gene or gene family can be utilized as a molecular indicator of identity.

Methods for detecting the polymorphic polynucleotide sequences that are molecular indicators of identity include, in addition to T-RFLP method described above: restriction fragment length polymorphisms (RFLP), amplified fragment length polymorphisms (AFLP), allele specific hybridization (ASH), amplified variable sequences, randomly amplified polymorphic DNA (RAPD), self-sustained sequence replication, simple sequence repeat (SSR), single nucleotide polymorphism (SNP), and single-strand conformation polymorphisms (SSCP).

Procedures for detecting polymorphic polynucleotide sequences can be based on the physical properties of the nucleic acids. For example, polymorphic polynucleotides can be distinguished based on hybridization to a probe nucleic acid. Hybridization can be performed with the probe and target nucleic acids in solution, for example, followed by capture of the duplexed nucleic acid. More commonly polymorphic polynucleotides are detected by hybridization methods in which the probe or the target nucleic acids is attached to a solid phase, such as a membrane, a "chip" (for example, a glass or plastic microarray) or a column or other substrate. For example, the target polymorphic polynucleotide can be detected by hybridization of a labeled DNA (or even an RNA) probe. Similarly, the target polymorphic polynucleotide can be DNA, e.g., genomic DNA, cDNA or amplification products, or can be RNA.

Hybridization of nucleic acids is dependent on a variety of parameters, including for example, the length, degree of complementarity, nucleotide sequence composition (e.g., GC v. AT content), and nucleic acid type (e.g., RNA versus DNA). In general, the more similar the sequences of the two nucleic acids are, the more stringent the conditions at which they will hybridize. The stringency of hybridization conditions are sequence-dependent and are different under different environmental conditions. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y. (2001); Tijssen, *Hybridization With Nucleic Acid Probes, Part I. Theory and Nucleic Acid Preparation*, Laboratory Techniques in Biochemistry and Molecular Biology, Elsevier Science Ltd., NY, N.Y. (1993). and Ausubel et al., *Short Protocols in Molecular Biology*, 4th ed., John Wiley & Sons, Inc. (1999).

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of ordinary skill in the art can readily determine variations on these conditions. Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Amplification products can be produced using a variety of well-known protocols. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. Numerous procedures for PCR are known in the art and exemplary protocols can be found, e.g., in Sambrook and Ausubel (supra). The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134, which are incorporated by reference herein.

Such protocols include methods for amplifying target polymorphic polynucleotides using universal primers that recognize a conserved sequence common between species, which flank a polymorphic region suitable as a molecular indicator of identity. Alternatively, amplification can be performed using sequence specific or selective primers that hybridize to and selectively amplify only one (or a subset) of target polymorphic polynucleotides. Optionally, a quantitative amplification (quantitative PCR method can be utilized). Frequently, amplification products can be directly detected (that is detected without the need to hybridize a labeled probe). For example, amplification products are commonly produced from nucleic acids derived from samples of microorganisms in sufficient quantity that they can be visualized directly, for example, following size separation by electrophoresis on an agarose or acrylamide gel. Optionally, the amplification products can be treated with a restriction enzyme, e.g., as described above with respect to detection of T-RFs.

Alternatively, a molecular indicator of identity can be detected in situ, without isolating or otherwise preparing a nucleic acid from the sample of microorganism. For example, amplification methods can be adapted to in situ procedures, in which the molecular indicator of identity is amplified while still located in the cell of the microorganism, e.g., utilizing labeled primers that result in a product detectable optically or autoradiographically.

Alternatively, the molecular indicator of identity can be detected by determining the nucleotide sequence of a portion of the microbial genome. Typically, the portion of the microbial genome includes one or more polymorphic polynucleotides, such as the 16S rRNA gene or any of the alternative phylogenetically informative genes discussed above. Methods for determining the nucleotide sequence of a nucleic acid are well established in the art. Additionally, numerous kits are available for manual and/or automated sequencing of nucleic acids. For example, a polynucleotide sequence can be determined, e.g., using the Sanger dideoxy termination method (Sanger et al., *Proc Natl Acad Sci USA* 74:5463-7 (1977)), the polymerase chain reaction, in vitro transcription and reverse transcription. Commercially available kits and reagents for performing sequencing are readily available and included, e.g., SUPERSCRIPT™ (Life Technologies, Rockville, Md.); and heat stable THERMO SEQUENASE® (LiCor, Lincoln, Nebr.).

V. Categorization of Microbial Communities

Identification of the predominant species of microorganisms among subjects in a population makes it possible to determine consensus profiles defining groups or subsets within the sampled group. More particularly, by identifying the predominant species of microorganisms inhabiting the vaginas of women without vaginal pathology, that is "healthy" or "normal" women (with respect to vaginal health or disease), categories of consensus profiles corresponding to normal vaginal microbiota have been identified. However, it should be noted that the methods described herein with respect to the identification of categories of normal vaginal microbiota are broadly applicable to the identification of categories of microorganism from essentially any sample or environment. For example, categories of abnormal vaginal microbiota, that is microbial populations present in the vaginas of women with symptoms of a vaginal pathology, also can be identified.

Categories defined by microbial consensus profiles can be differentiated using any of a variety of clustering algorithms and methodologies. In general, clustering (or cluster analysis) is a type of unsupervised learning in which the classes are unknown a priori and the goal is to discover these classes from data. For example, in the context of the present disclosure, categories of normal vaginal microbiota are differentiated from among microbial profiles obtained from samples from women without vaginal pathology.

Clustering involves several distinct steps: 1) defining a suitable distance between objects, and 2) selecting and applying a clustering algorithm. Clustering procedures commonly fall into two categories: hierarchical methods and partitioning methods. Hierarchical methods can be either divisive (top-down) or agglomerative (bottom-up). Hierarchical methods provide a hierarchy of clusters, from the largest, where numerous objects are in one cluster, through to the smallest, where each object is in its own cluster.

Partitioning methods usually require the specification of the number of clusters. Then, a mechanism for apportioning objects to clusters must be determined. These methods partition the data into a pre-specified number, k, of mutually exclusive and exhaustive groups. The method iteratively reallocates the observations to clusters until some criterion is met (e.g. minimize within-cluster sums-of-squares). Examples of partitioning methods include k-means clustering, partitioning around medioids (PAM), self organizing maps (SOM), and model-based clustering.

Typically, most methods used in practice are agglomerative hierarchical methods, in large part due to the availability of efficient algorithms. Advantages of hierarchical methods include fast computation, whereas their disadvantages include that they are rigid and cannot be corrected later for erroneous decisions made earlier in the method.

In contrast, partitioning advantages include the ability to provide clusters that (approximately) satisfy an optimality criterion, whereas disadvantages include the requirement that an initial k be specified and that the methods require lengthy computations.

Determining a meaningful number of clusters is an important aspect of cluster analysis. This problem has been studied rigorously in the statistical literature (Cooper & Milligan (1984); Milligan & Cooper, *Psychometrika* 50: 159-179 (1985)). Milligan & Cooper (1985) used simulations and four hierarchical clustering methods to compare thirty methods for estimating the number clusters in a population (*SAS manual* (1996)). Their results favor three criteria (*SAS Manual* 1996): the Cubical Clustering Criterion (CCC) introduced by Sarle *The Cubic Clustering Criterion*. SAS Institute (1983); pseudo F introduced by Calinski & Harbasz (*Communications in Statistics* 3:1-27 (1974)); and a statistic that can be transformed to pseudo $T^2$ developed by Duda & Hart *Pattern Classification and Scene Analysis* John Wiley & Sons, Inc., New York (1973).

For example, the cubical clustering criterion (CCC) of Sarle can be used to identify the optimum number of clusters in a population, and is a suitable method for determining consensus profiles. This approach compares the $R^2$; the proportion of variance accounted for by the clusters—to the expected value of the $R^2$ calculated under the assumption that the data come from a uniform distribution based on a hyperbox. The optimal number of clusters is identified by plotting the CCC index against the number of clusters, and then locating the number of clusters that has the highest positive index value that is greater than 2. Peaks between 0 and 2 indicate possible clusters. Negative values that are decreasing for one or more clusters indicate unimodal or long tailed distribution of the data. Extreme negative values indicate the presence of outliers. The following equation shows the CCC index as presented by Sarle (*SAS Technical Report* A-108, SAS Institute Inc., Cary N.C. (1983)):

$$CCC = \ln\left[\frac{1-E(R^2)}{1-R^2}\right]\frac{\sqrt{\frac{np^*}{2}}}{(0.001+E(R^2))}$$

Another exemplary method for determining consensus profiles of normal vaginal microbiota is the pseudo F index (Calinski & Harabasz, supra). The pseudo F index is calculated as follows:

$$F = \frac{\text{trace}[B/(k-1)]}{\text{trace}[W/(n-k)]}$$

where n is the number of individuals in a sample, k is the number of clusters, B is the between cluster sum of squares and cross product matrix, and W is the pooled within cluster sum of squares and cross products matrix. Identification of the optimal number of clusters using this method also involves plotting the F index against the number of clusters. The number of clusters associated with the maximum of the index is the optimal number of clusters.

Yet another exemplary clustering method is the ratio index of Duda & Hart (supra). A ratio index (Je(2)/Je(1)) can be used to identify the optimum number of clusters in a data set. Je(2) is the within cluster sum of squared error when the data is divided into two clusters. Je(1) is the sum of squared error before division. If the within cluster sum of squared error for the two clusters is less than that for one cluster (within a certain critical value), the one cluster hypothesis is rejected in favor of two clusters. This test can be transformed to a pseudo $T^2$ test (Johnson, *Applied multivariate methods for data analysis*, SAS Institute (1998); *SAS Manual* (1996)). To determine the optimal number of clusters one looks for a small value for the pseudo $T^2$ followed by a large value (*SAS Manual* (1996)). This method can be only applied with hierarchical clustering methods (*SAS Manual* (1996)).

Alternatively, classification methods (or class prediction) can be utilized to determine normal classes of microbiota. Classification methods include principal component analysis, discriminant analysis (linear and quadratic discriminant), nearest neighbor classifiers (k-nearest neighbor), classification and regression trees (CART), evolutionary algorithms, neural networks and multinomial log-linear models, support vector machines, and aggregated classifiers (bagging, boosting, forests).

Within Cluster Sampling

Within cluster sampling is used to identify a number of communities within a cluster that properly represent the cluster so they can be used to construct clone libraries. Several methods can be used to identify appropriate communities. Two of these methods (The Pair-wise Distances method and the Maximum Variation method) utilize the coefficient of variation (CV) as a decision rule to determine the sample size. The coefficient of variation is given in the following equation:

$$CV = \frac{\text{Standard Error}}{\text{mean}} = \frac{(\text{Standard Deviation})/\sqrt{n}}{\text{mean}}$$

where n is the sample size. The other two methods (the Systematic Cover and the Cover sampling methods) use the percent cover as a decision rule to determine the appropriate sample size. The cover is defined as the proportion of phylotypes that might be detected in a sample as compared to the total number of phylotypes detected in the whole cluster. Detailed description of each one of these methods is provided below.

The selection of methods depends on the amount of variation in the cluster. The lowest resolution results from using the Systematic Cover method, which focuses on richness alone in choosing a sample. The aim of this method is to identify the species that make up the communities associated with a certain cluster with no regard to how abundant these species might be. The advantage is that smaller sample sizes will be chosen using this method as compared to the other methods. The highest resolution results from choosing a sample using the Maximum Variation method, which is directed at explaining as much of the variation in the cluster as possible with a disadvantage of having to deal with large sample sizes compared to the other methods. The Pair-wise Distances method and the Cover Sampling method provide intermediate resolutions. The Maximum Variation, Pair-wise Distances, and Cover Sampling methods also provide samples that help the practitioner study the abundance of the different species that a cluster is composed of, in addition to identifying which species are present.

All of these methods are based on the assumption that every cluster represents a separate true community type (an ideal community made up of all the species that can be seen in the sampled microbial communities that belong to that cluster, it can be thought as the representative microbial community of a certain cluster) and communities that belong to that cluster constitute all possible sample microbial communities of that community type. Given this assumption, the true vector of means and the true variance-covariance matrix of the peak vectors is obtained. Complete cover (100%) can be attained if all communities within a given cluster are sampled.

Pair-Wise Distances.

Given the assumption that a cluster contains all possible communities that belong to a certain community type, the true mean pair-wise distance for any cluster is known, and equal to the mean of the pair-wise distances between the communities forming that cluster. The following is an iterative approach to determine the sample size that conforms to a predefined coefficient of variation.

1) Sample n communities repeatedly B times at random without replacement from all communities within a cluster. Because at least two communities are needed to calculate pair-wise distances, n should be greater than or equal to 2.
2) Calculate the pair-wise distances between the sampled communities and average the results for each of the samples drawn.
3) Calculate the CV associated with the sample size n.
4) Repeat 1 through 3, adding 1 to the previous sample size, until the coefficient of variation is less than or equal to the predefined lower limit for the coefficient of variation.

The n resulting after the last step is the minimum sample size needed to attain a CV equal or less than a predetermined value. Ideally, the sampling distribution for the mean pair-wise distances is constructed based on all possible permutations at each sample size of interest and calculate the standard error based on these permutations. This can be computationally prohibitive. The proposed sampling without replacement approximates this sampling distribution and is less computationally intensive. The larger the number of repetitions (B), the more accurate the approximation will be.

Maximum Coefficient of Variation.

In this method the fragment length with the maximum coefficient of variation are used to calculate the sample size. This process identifies a sample that explains as much of the maximum variability as possible. A sampling without replacement algorithm similar to the one described above is used.

1) Calculate the CV corresponding to the peaks associated with each of the fragment lengths in a cluster.
2) Identify the fragment length that has the highest CV.
3) Repeatedly sample n communities B times, at random without replacement, from all communities within a cluster.
4) Calculate the CV, for the fragment length identified in step 2, associated with the sample size n.
5) Repeat steps 3 and 4, adding 1 to the previous sample size until the coefficient of variation is less than or equal to the predefined coefficient of variation.

Systematic Cover Method.

In this method, the communities are systematically searched until samples are identified that provide at least a predefined cover within each cluster. The following steps are included in this algorithm.

1) Find the community that provides the largest cover. This community will serve as a starting point.
2) Search for the second community that, when combined with the first, will again provide the largest cover.
3) Repeat this last step until the cover of the level of interest is attained.

As indicated above, this method provides the best cover though it might not provide the right representation of the phylotype abundance in a community type. However, the advantage of this method is that it provides the smallest sample size (with respect to number of communities) needed to identify the make up of a certain community type within a defined cover.

Cover Sampling Method.

This method aims to adjust the previous method to provide a viable representation of phylotype abundance in the different community types. Two stopping rules are employed for this purpose: The first is the cover (described in the previous method); the second is the frequency of attaining this cover when randomly choosing a certain number of communities (a sample size) that belong to a cluster. The aim is to choose a random sample size that covers a proportion, $\beta$, of the phylotypes in a cluster with frequency $\pi$ (95% for example). Similar to the methods presented under the coefficient of variation approach, all permutations of sampled communities need to be found based on a certain sample size to create the distribution of the covers associated with that sample size. A sampling without replacement strategy is also used to approximate such a distribution in this case. The sample size that meets the two rules is chosen as the optimum sample size. The algorithm is as follows:

1) Repeatedly sample n communities B times, at random without replacement, from all communities within a cluster.
2) The algorithm presented previously (see systematic method) is used to calculate the cover for each of the β samples.
3) The calculations are stopped if the proportion of times that the sample cover exceeds the predefined cover, β, is more than or equal π. Otherwise, steps 1 and 2 are repeated after increasing n by 1.

Sampling Intensity

A method was developed to identify a lower bound on the number of microbial communities sampled so that all common microbial community types are represented with high probability. For illustrative purposes we denote a community type as "common" if its frequency among the microbial community types is greater than or equal to $p_0=10\%$.

The largest sample size will be required when all of the common microbial community types are barely above the threshold required to be deemed common. For example, this occurs in the hypothetical when there are 10 common community types each with frequency of 10 percent. Any other configuration has fewer common community types and the common types would appear in higher frequency.

With respect to a sample of size n from a group of community types with 10 types of equal frequency: The probability that a particular community type is not sampled in the first draw is 0.90, and the probability that this type is missed in all n draws from the population is $(0.90)^n$, and therefore the chance that at least one of the 10 community types is missed in each of the n draws is bounded above by $(10)(0.90)^n$, making the chance that all the common types are sampled to be at least $1-(10)(0.90)^n$. Setting this probability equal to 0.99, virtually assures that all the common types will be sampled. This is done by solving for n in the following equation $(10)(0.90)^n=0.01$, which implies that $$n = \frac{\ln(.01/10)}{\ln(.90)} \approx 65.$$

In general, if $p_0$ is the minimum frequency of a common community type and $1-\alpha$ is the probability that all the common types are sampled, then the general formula for the sample size n is given by $$n = \frac{\ln(\alpha p_o)}{\ln(1 - p_o)}.$$

Yu and Williams (*Biotech* 10:776-777 (1991)) present a special case of this sampling formula that is concerned with one community type only. While the above formula virtually guarantees that all common types will be represented in the sample, it does not make any predictions about the sample frequency of each of these types. It is possible that a common type will appear in the sample with low frequency, simply due to sampling error. It is relatively straightforward to demonstrate that any type whose frequency in the population is 10% or higher, will appear in the sample (with 0.95 probability) at frequency of 4% or higher. The general inclusion rule, would be to include all types with sample frequency $\hat{p}$ or higher where $$\hat{p} = p_o - 1.645\sqrt{\frac{P_o(1 - p_o)}{n}}.$$

Following selection of samples, according to this within cluster analysis, the samples are further analyzed to identify consensus profiles of normal vaginal microbiota. In one favorable embodiment, the samples are analyzed in an automated analysis pipeline, as described below.

VI Automated Analysis Pipeline

In order to process large numbers of samples in a labor and cost effective manner, it is desirable that an automated processing and analysis procedure be employed. For example, to determine consensus profiles of normal vaginal microbiota, samples of microorganisms obtained from women without vaginal pathology can be systematically analyzed to determine the predominant species of microorganisms. Conversely, samples of microorganisms can be analyzed from women with symptoms or signs of a pathological condition to determine consensus profiles corresponding to, e.g., a vaginal pathology. For example, the 16S rRNA gene sequences can be analyzed in an automated process using a "ribosomal RNA analysis pipeline." The ribosomal RNA analysis pipeline is a high-throughput program that transforms raw sequence data into an easily interpretable output. This pipeline first identifies high quality sequences (generally, greater than 500 bp), having less than 3% uncalled bases. The sequences are then used as query sequences to search for the 25 most similar ribosomal RNA sequences of eubacterial species and one archaebacterial species obtained from the Ribosomal Database Project (RDP) using the BLAST algorithm. Sequences taken from the RDP database are selected to be at least 1200 bp long. The RDP sequence for the closest relative of each input sequence is included in subsequent analyses. All of the input sequences used in the BLAST search, their closest relatives and a set of 39 bacterial rRNA sequences representing a broad range of Eubacterial sequences, plus a single Archaea sequence are aligned using ClustalW. The polynucleotide sequence of the aligned region and the genetic distances between the individual sequences can then be determined (e.g., by the Jukes and Cantor method). The sequences are then clustered based upon these genetic distances using the neighbor joining method as implemented in the GCG 19 (Accelrys Inc., San Diego, Calif.) programs "distances" and "growtree." The resulting distance matrix is used to compute the following statistics on groups of sequences that had the same closest relative in the RDP type strain database: the mean and standard deviation of the sequence divergence within such a group; and the mean and standard deviation of the sequence divergence of all sequences in that group compared to their common closest RDP type strain relative. The program Statgen can be employed to compute these statistics, and is available by contacting Celeste Brown (celesteb@uidaho.edu).

Using the methods described herein, normal vaginal microbiota can be determined for any group or population of women (or female animals). For example, normal vaginal microbiota can be determined among groups of women categorized by racial, ethnic, demographic, geographic or other indicators. Normal vaginal microbiota can be determined in a selected population (or first population) of women, such as a population of women selected from a racially or ethnically defined population of women. Normal vaginal microbiota can also be determined from a different (or second or subsequent)

population of women, such as a different racially or ethnically defined population or a population defined by alternative criteria (such as geographic or other demographic, e.g., age, sexual activity). Optionally, the microbiota profiles and/or categories of the first and second populations of women can be compared. Likewise, using the methods described herein, abnormal microbial populations can be identified, e.g., in women with a specified vaginal pathology, such as BV.

Using these methods the following exemplary categories of normal vaginal microbiota were identified in Caucasian women:

I) *Lactobacillus iners;*
II) *Lactobacillus crispatus;*
III) *Lactobacillus crispatus* and *Lactobacillus jensenii;*
IV) *Lactobacillus iners, Lactobacillus crispatus* and *Lactobacillus gasseri;*
V) *Atopobium vaginae* and one or more species of the order Clostridiales;
VI) *Lactobacillus crispatus* and *Lactobacillus gasseri;* and
VII) *Lactobacillus crispatus, Lactobacillus iners* and *Lactobacillus jensenii.*

Additionally, individuals with vaginal microbiota predominated by *Streptococcus* sp., *Veillonella* sp., and *Gemella palaticanis; Streptococcus* sp., or *Lactobacillus gasseri* were identified.

Categories of normal vaginal microbiota can similarly be identified among women of different ethnic and racial backgrounds. An overlapping set of bacterial phylotypes are found in normal women of African ancestry, with five categories predominating:

I) *Lactobacillus iners;*
II) *Lactobacillus crispatus;*
V) *Atopobium vaginae* and one or more species of the order Clostridiales;
VIII) *Lactobacillus gasseri;* and
IX) *Megasphaera* sp. and one or more species of the order Clostridiales.

Numbering is kept consistent with the major categories observed in Caucasian women to facilitate comparison.

Additional microbial profiles observed in women of African ancestry include *Lactobacillus gasseri, Gardinerella vaginalis* and *Streptococcus* sp.; *Escherichia coli* and *Shigella* sp.; *Lactobacillus jensenii* and *Streptococcus* sp.; and, *Gemella palaticanis* and *Mycoplasma* sp. These species include: *Peptoniphilus* sp., *Anaerococcus tetradius, Micromonas* sp., *Dialister* sp., *Aerococcus* sp., *Veillonella* sp., *Finegoldia magna, Granulicatella elegans, Clostridium perfringens, Mobiluuncus mulieri, Peptostreptococcus anaerobius, Pseudomonsa* sp., uncultured *Mycoplasma* sp (GENBANK® Accession No. S000123722), uncultured bacterium (GENBANK® Accession No. S000329832) and additional uncultured species represented by GENBANK® Accession Nos. S000126539, S00343908, S000343909, S000343911, S000245992, and a species previously not identified in vaginal samples represented by GENBANK® Accession Nos. S000350386.

VII. Assignment of Microbiota Profiles to a Category

Once categories of normal microbiota have been identified within a population of subjects, the categories provide a valuable diagnostic guideline for the evaluation of subjects with respect to health and disease status. For example, following characterization of categories of vaginal microbiota in women without a vaginal pathology ("normal" women) using the clustering methods described above, samples can be assigned to identified categories based on the presence and prevalence of particular species of microorganisms in a sample.

Because an individual woman is expected to maintain a relatively stable microbiota profile over time, a baseline sample obtained during routine gynecological exam can be utilized to determine the category of vaginal microbiota that is normal for the particular woman. Such a baseline profile provides a convenient comparison in the event that the subject presents with symptoms of a condition affecting vaginal health. Even in the absence of a baseline profile, the recognition of these normal profiles makes it possible to provide a more accurate diagnosis with respect to conditions that interfere with a normal vaginal ecology.

Additionally, the recognition of multiple categories of normal microbiota makes it possible to develop and select probiotic regimens suitable for maintaining normal microbiota (for example, by prophylactic administration) and treating disruptions in the normal vaginal microbiota that are specific for the microbial ecology of a particular subject, and thus, more likely to exert a long-term beneficial effect. Thus, a probiotic regimen can be selected for a particular subject based on her baseline "normal" profile. By identifying the predominant species of microbiota present in the subject's vagina under normal conditions and assigning the profile to one of the predefined categories of normal vaginal microbiota, it is possible to select a probiotic regimen that is specifically designed to maintaining and/or restoring the healthy vaginal microbiota of the subject.

VIII. Diagnostic Reagents and Kits

Based on the identification of species of microorganisms present in the vagina under normal health conditions, primers and probes are provided that greatly simplify the detection and categorization of vaginal microbiota. Using probes and/or primers specific for the species of microorganisms present in the vagina under normal condition, the vaginal microbiota can be quickly and effectively categorized to, for example, generate a baseline microbial profile. Accordingly, primers and probes specific for the predominant species of normal vaginal microbiota are a feature of the invention. Similarly, kits including multiple primers and/or probes useful for detecting multiple species of microorganisms, such as the predominant species that define categories of normal vaginal microbiota, are a feature of the invention. The primers and probes can be utilized in a wide variety of methods and protocols, including the hybridization and amplification methods described above. Optionally, the primers and probes can be immobilized onto a substrate, such as an array, e.g., a microarray on a glass or plastic matrix, chip or slide. Exemplary primers and probes are provided in the Examples section below, e.g., in Table 4.

Generally, the kits described herein are optionally packaged to include reagents for preparing nucleic acids or proteins, amplifying nucleic acids, and/or detecting nucleic acids or other biomolecules. For example, the kits optionally include assay components, such as buffers, reagents, enzymes, serum proteins (such as antibodies), receptors, etc., for detecting microorganisms normally present in the vagina. Optionally, additional probes and/or reagents are included for detecting pathological organisms such as yeast (*Candida albicans*) or pathogenic bacteria. In the case of prepackaged reagents, the kits optionally include pre-measured or pre-dosed reagents that are ready to incorporate into the assay methods without measurement, e.g., pre-measured fluid aliquots, or pre-weighed or pre-measured solid reagents that can be easily reconstituted by the end-user of the kit. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a bead, a gel, etc.), lyophilization, or the like.

Such kits also typically include appropriate instructions for using the probes and reagents, and optionally for preparing samples and the like. The various elements of the kits are typically packaged together in a single package or set of related packages.

When utilizing a plurality of probes, for example, a plurality of probes each of which is specific for a species of normal vaginal microbiota, such as those described in the Examples, the probes can be arranged in an ordered liquid or solid array. Optionally, the array also includes probes that are specific for pathogenic microorganisms (usually organisms that cause a pathology of the vagina). A wide variety of array formats can be employed in accordance with the present disclosure. One example includes a linear array of oligonucleotide bands, generally referred to in the art as a "dipstick." Another suitable format comprises a two-dimensional pattern of discrete cells (e.g., 96 squares in a 8 by 12 array). As would be readily appreciated by those skilled in the art, other array formats including, but not limited to, slot (rectangular) and circular arrays are equally suitable for use (see U.S. Pat. No. 5,981, 185). In one embodiment, the array is formed on a polymer medium, which is a thread, membrane or film. An example of an organic polymer medium is a polypropylene sheet having a thickness on the order of about 1 mil (0.001 inch) to about 20 mil, although the thickness of the film is not critical and can be varied over a fairly broad range. Particularly disclosed for preparation of arrays at this time are biaxially oriented polypropylene (BOPP) films; in addition to their durability, BOPP films exhibit a low background fluorescence.

The arrays of the present disclosure can be included in a variety of different formats. A "format" includes any item to which the solid support can be affixed, such as microtiter plates, test tubes, inorganic sheets, dipsticks, and the like. For example, when the solid support is a polypropylene thread, one or more polypropylene threads can be affixed to a plastic dipstick-type device, polypropylene membranes can be affixed to glass slides, etc. The particular format is, in and of itself, unimportant. All that is necessary is that the solid support can be affixed thereto without affecting the functional behavior of the solid support or any biopolymer absorbed thereon, and that the format (for example, the dipstick or slide) is stable to any materials into which the device is introduced (for example, clinical samples, hybridization solutions, and the like).

IX. Probiotic Formulations

Previous studies done using cultivation-dependent methods have shown that *L. jensenii, L. acidophilus* and *L. casei,* and *L. gasseri* are the dominant species in the human vagina (Reid et al. *FEMS Immunol Med Microbiol* 15:23-26, 1996), while others have reported that *L. acidophilus, L. rhamnosus,* and *L. fermentum* are the most common species (Hughes et al., *Obstet Gynecol* 75:244-248,1990; Reid et al., *FEMS Immunol Med Microbiol* 35:131-134, 2003). The correlation between the occurrence of high numbers of lactobacilli and the absence of BV or yeast infections has inspired efforts to use lactobacilli as probiotics. Indeed, the age-old practice of a vaginal instillation of yogurt has the same premise. Efforts to use *L. crispatus* and *L. jensenii*, or *L. rhamnosus* and *L. fermentum* as probiotics have met with mixed results. Other commercially available probiotic preparations such as Lactobac, which contains *Lactobacillus rhamnosus* and *Bifidobacterium longum*, or Femilac, which contains *L rhamnosus, L delbrueckii, L. acidophilus*, and *Streptococcus thermophilus*, were also shown to be not effective. This failure is likely to be due at least in part to differences in the composition of vaginal communities between women.

Based on the identification of novel groups of normal microbiota described herein, and the ability to classify vaginal microbiota according to these groups, it is possible to design probiotic regimens and formulations to maintain and reestablish the microbial community that is normal or healthy for a particular woman. Although probiotic treatment has been advocated for the maintenance of a healthy vaginal microbiota, until the present disclosure, it has not been possible to tailor the probiotic regimen to the specific species of microbiota that are healthy for a particular individual. For example, douching with yogurt containing *Lactobacillus* species has been a common folk remedy for the treatment of yeast infections. More recently, it has been suggested that particular strains of *Lactobacillus*, such as *Lactobacillus rhamnosus* GR-1 and *Lactobacillus fermenturm* RC-14 can be used to cure yeast infections and reduce the risk of viral infections (see, e.g., U.S. Patent Application no. 20040022775).

The present disclosure extends these findings, and makes it possible to select and administer probiotic formulations and regimens that not only reassert a desirable microbial community, but reestablish a microbial profile that closely resembles the normal microbial community of the particular subject, and is likely to be maintained in the long term based on the subject's personal physiology. Accordingly, a probiotic formulation is administered to a subject, either prophylactically or therapeutically, that includes at least one composition that promotes growth of one or more species of microorganisms selected from a normal vaginal microbiota. The probiotic regimen typically includes one or more species of microorganisms, and, optionally, one or more pharmaceutical or nutritional composition that promotes growth of the selected microorganism(s).

Based on the category of microbiota normally present in a woman, a probiotic regimen is selected that corresponds to the microorganisms corresponding to the consensus profile defining the category of normal microbiota. For example, the realization that bacterial species other than *Lactobacillus* sp. are important in the vaginal microbiota of healthy women supports the utilization of species other than *Lactobacillus* in probiotic formulations. For example, in women whose vaginal microbiota include *Atopobium vaginae*, this species of microorganism can be favorably employed in a probiotic regimen. Similarly, based on the disclosure provided herein, a suitable probiotic regimen can be selected for essentially any subject once her normal vaginal microbiota is ascertained and categorized.

For example, when selecting a probiotic regimen for treatment of Caucasian women, the probiotic regimen is typically selected to promote the growth of microorganisms in one of the following supergroups common among Caucasian women:

I) *Lactobacillus iners;*

II) *Lactobacillus crispatus;*

III) *Lactobacillus crispatus* and *Lactoba cillus jensenii;*

IV) *Lactobacillus iners, Lactobacillus crispatus* and *Lactobacillus gasseri;*

V) *Atopobium vaginae* and one or more species of the order Clostridiales;
VI) *Lactobacillus crispatus* and *Lactobacillus gasseri*; and
VII) *Lactobacillus crispatus, Lactobacillus iners* and *Lactobacillus jensenii*.

When selecting a probiotic regimen for treatment of a woman of African ancestry, the probiotic regimen is typically selected to promote the growth of microorganisms in on of the following supergroups common among African-American women:

I) *Lactobacillus iners;*
II) *Lactobacillus crispatus;*
V) *Atopobium vaginae* and one or more species of the order Clostridiales;
VIII) *Lactobacillus gasseri;* and
IX) *Megasphaera* sp. and one or more species of the order Clostridiales.

Of course, probiotic regimens for promoting establishment, growth or maintenance of other species identified as constituents of normal vaginal microbiota, including species disclosed herein as constituents of the normal vaginal microbiota of a single subject can also be selected and administered. Likewise, probiotic regimens that correspond to species of microorganisms present in categories of normal vaginal microbiota of other populations of women can be selected.

Thus, a monoculture (for example, a monoculture of *Atopobium vaginae*) or mixed culture of microorganisms can be introduced into a subject to affect the subject beneficially. For example, to assert of beneficial effect upon vaginal health, a culture of microorganisms is introduced into the vagina of a subject. Following colonization of the vagina, the introduced species of microorganism(s) reduce vaginal pH, secrete a variety of metabolites which provide beneficial effects, and are non-toxic to the host.

The selected microorganisms can be aerobically, microaerophillically or anaerobically grown using any appropriate growth medium typically used to culture the species of bacteria. For example, the cultures can be grown in LB broth, TB broth, MRS broth or the like. The resulting cultures can be vaginally instilled as viable whole cells. Such vaginally administered microorganisms can colonize the human urogenital tract, thereby reasserting a normal vaginal microbiota and eliminating undesirable microorganisms such as pathogenic bacteria, yeast and viruses. The vaginally administered microorganisms also stimulate the indigenous normal flora of the urogenital tract, thereby preventing, treating and/or reducing the occurrence of infections caused by pathogenic bacteria, yeast and viruses.

Although this invention is not intended to be limited to any particular mode of application, one favorable route is vaginal administration of the compositions. Where multiple species of microorganisms are present in a group, the microorganisms can be administered together, substantially simultaneously, or sequentially. The microorganisms can be administered by any method now known or hereafter developed, including but not limited to, in the form of tablet, pill or capsule. One exemplary form of application involves the preparation of a freeze-dried capsule comprising the composition of the present invention. Another exemplary form of application involves the preparation of lyophilized cells within a capsule. Still another exemplary form of application involves the preparation of a heat dried cells within a capsule.

Such a capsule contains an effective amount of the microorganism to achieve a beneficial effect without causing significant side effects. An effective amount of the microorganism will vary with the particular goal to be achieved, the age and physical condition of the patient being treated, her race, ethnicity, geographic location, etc., and the severity of the underlying disease, the duration of treatment, the nature of concurrent therapy and the specific microorganism employed. For example, a capsule comprising about $10^9$ microorganisms is suitable. The capsule can contain one single or two or more different species of microorganisms and can additionally include by-products (e.g., metabolites) thereof.

Alternatively, an effective amount of the selected microorganisms can be administered in a liquid formulation. For example, viable or non-viable whole cells can be administered in phosphate buffered saline ("PBS") solution, or in a suspension of microbial nutrients.

Alternatively, a biologically compatible device can be coated or impregnated with an effective amount of the selected microorganisms and inserted into the urogenital tract. For example, the effective amount of microorganisms can be deposited on the outer surface or the inner surface of the biologically compatible device, in a uniform or non-uniform manner. The biologically compatible device can be composed of polymers such as cellulose polymers (for example, modified cellulose polymers such as those commonly used in tampons), fluorinated ethylene propylene, sulfonated polystyrene, polystyrene, polyethyleneterephthalate silicone, polyurethane, polyvinylchloride silicone rubber, or glass. The device can be a catheter such as a urinary or peritoneal catheter, a diaphragm, a stent, an IUD, a tampon, a pad (such as a sanitary pad) a diaper, an intravenous line, a peritoneal dialysis tube, an endotracheal tube, or an intravaginal, intrauterine, or intraurethral or intraureteral device.

The microorganisms can be coated by, or administered with, a material to prevent or reduce inactivation by endogenous enzymes. For example, the selected microorganisms can be co-administered with enzyme inhibitors or in liposomes. Enzyme inhibitors include pancreatic trypsin inhibitor, diisopropylfluorophosphate (DFP) and trasylol. Liposomes include water-in-oil-in-water P40 emulsions as well as conventional and specifically designed liposomes which transport lactobacilli or their by-products to the urogenital surface. Dispersions also can be prepared, for example, in glycerol, liquid polyethylene glycols, and mixtures thereof, and in oils.

The pharmaceutical forms suitable for vaginal instillation also include sterile aqueous solutions (where water soluble) or dispersions and sterile powders for the extemporaneous preparation of sterile solutions or dispersions. The pharmaceutical forms for vaginal instillation must be stable under the conditions of manufacture and storage. The carrier can be a solvent or dispersion medium containing, for example, water, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride.

The selected microorganisms conveniently can be formulated into capsules or suppositories and can also contain the following: a binder, such as gum tragacanth, acacia, corn starch or gelatin; excipients such as dicalcium phosphate; a disintegrating agent such as corn starch, potato starch, alginic acid, and the like; a lubricant such as magnesium stearate, and combinations thereof. When the dosage unit form is a capsule, it can contain, in addition to materials of the above type, a liquid carrier. Various other materials can be present as coatings or to otherwise modify the physical form of the dosage unit. For instance, capsules or lactobacilli in suspension can be coated with shellac, sugar or both.

The selected microorganisms are compounded for convenient and effective administration in effective amounts with a suitable pharmaceutically acceptable carrier in dosage unit form as hereinbefore disclosed. A unit dosage form can, for example, contain the principal active compound in an amount approximating at least $10^9$ viable cells.

The pharmaceutically acceptable carrier can be in the form of milk or portions thereof including yogurt. Skim milk, skim milk powder, non-milk or non-lactose containing products also can be employed. The skim milk powder is conventionally suspended in phosphate buffered saline (PBS), autoclaved or filtered to eradicate proteinaceous and living contaminants, then freeze dried, heat dried, vacuum dried, or lyophilized. The carrier should be prepared to maximize the acidic effect of the selected microorganisms.

Some other examples of substances which can serve as pharmaceutical carriers are sugars, such as lactose, glucose and sucrose; starches such as corn starch and potato starch; lactic acid, bacteriocin; cellulose and its derivatives such as sodium carboxymethycellulose, ethylcellulose and cellulose acetates; powdered tragancanth; malt; gelatin; talc; stearic acids; magnesium stearate; calcium sulfate; calcium carbonate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; cranberry extracts and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, lubricants, excipients, tabletting agents, stabilizers, anti-oxidants and preservatives, can also be present.

X. Vaginal Expression of Recombinant Nucleic Acids

The categorization of normal vaginal microbiota as described herein makes it possible to select microorganisms optimal for use as vectors to direct expression of recombinant nucleic acids in the vagina. Expressing products of recombinant nucleic acids, e.g., recombinant proteins and RNA molecules, in the vagina is useful for a variety of prophylactic and/or therapeutic applications. For example, expression of CD4 by Lactobacillus jensenii in the vagina has been suggested to reduce the risk of infection by HIV (Chang et al. Proc. Natl. Acad. Sci. USA 100: 11672-11677 (2003)). Similarly, other binding proteins, e.g., receptors, can be expressed to inhibit infection by other viruses and pathogens. Antigenic polypeptides and proteins can be expressed in the vagina to elicit an immune response, that is, as vaccines. Because the normal vaginal microbiota is stable over time, and is resistant to the introduction of foreign species, expression of the recombinant protein can be optimized by selecting as the host cell a species of microorganism that is normal for the particular subject, facilitating colonization of the vagina by the engineered microorganism. By selecting a host microorganism that is capable of successfully colonizing the vaginal environment of the particular subject, it is possible to achieve robust long term expression of the recombinant protein with minimal disruption to the native system.

For example, a species of microorganism is selected from among the categories of normal vaginal microbiota as described herein. A recombinant nucleic acid encoding a polypeptide or protein of interest operably linked to transcription regulatory sequences that are well expressed in the selected species of microorganism is introduced into the selected host microorganism. Alternatively, the recombinant nucleic acid can encode a therapeutically useful RNA molecule, such as an antisense RNA, an siRNA, or a ribozyme. The transcription regulatory sequence can include a promoter endogenous to the selected strain of microorganism or another promoter capable of directing high level expression of the linked polynucleotide sequence. Optionally, the nucleic acid also includes an origin of replication. The recombinant microorganism incorporating the heterologous nucleic acid encoding the protein of interest is introduced into the vagina where it replicates and expresses the recombinant protein.

EXAMPLES

Example 1

Categorization of Normal Vaginal Microbiota in Five Women

Cultivation-independent methods were used to analyze samples collected at multiple time points over a 2-month period from the mid-vagina of normal healthy women. The species composition and structure (proportion of each species) of each community was assessed.

In brief, total microbial community DNA was isolated from microbial cells that had been retrieved on vaginal swabs. Genomic DNA was isolated from 0.5 ml aliquots of the cell suspensions using a two-step cell lysis procedure. First, bacterial cell walls were disrupted enzymatically by the addition of mutanolysin (50 µg) and lysozyme (500 µg) followed by incubation for 1 hour at 37° C. Secondly, the cells were mechanically disrupted by 6 freeze-thaw cycles. Each cycle consisted of 2 minutes incubation at 100° C. that was immediately followed by 2 minutes in liquid nitrogen. Between each freeze-thaw cycle, the cell suspensions were incubated for 1 minute in an ultrasonic bath. Proteins in the disrupted cell suspension were digested with proteinase K (Qiagen, Hilden, Germany) during a 1-hour incubation at 55° C. Further isolation and purification of the total DNA extract was performed using the Wizard DNA purification kit (Promega, Madison, Wis., USA).

Samples were prepared for T-RFLP analysis as described above. In brief, the 16S rRNA genes in each sample were amplified using fluorescently labeled primers. Reaction mixtures for PCR contained 50 ng of genomic DNA, 5 µl of 10× buffer (500 mM KCl, 100 mM Tris-HCl (pH 9.0), and 15 mM MgCl2; Amersham Biosciences, Piscataway, N.J., USA); bovine serum albumin (BSA; 20 µg), each dNTP at a concentration of 200 µM (Amersham Biosciences), each primer at a concentration of 0.4 µM, and 1 U of Taq-polymerase (Amersham Biosciences) in a final volume of 50 µl. If PCR products were used for subsequent T-RFLP analysis, the forward primers 8f: 5'-agagtttgatcmtggctcag-3'(SEQ ID NO:1); and, 341f: 5'-cctacgggaggcagcag-3' (SEQ ID NO:2) were labeled with 5-carboxy-fluorescein (5-FAM) at the 5' termini, and the reverse primers: 926r: 5'-ccgtcaattcctttragttt-3' (SEQ ID NO:3); and, 1406r: acgggcggtgtgtrc-3' (SEQ ID NO:4) were labeled with 5' tetrachlorofluorescein (5-Tet) at the 5' termini (Eurogentec, Seraing, Belgium). The same primers without fluorescent labels were used for PCR reactions to generate target DNA for subsequent cycle sequencing reactions as described below. DNA amplification was performed with a Geneamp 9700 thermocycler (Perkin-Elmer, Norwalk, Conn., USA) using the following program: a 5 min initial denaturation at 94° C. followed by 30 cycles consisting of denaturation (1 min at 94° C.), primer annealing (1 min at 49.5° C. for the primer combination 341f-926r, and 1 min at 55° C. for the primer combinations 8f-926 and 8f-1406r), and primer extension (2 min at 72° C.). A final extension was performed at 72° C. for 10 min. Amplification of DNA was verified by electrophoresis of each PCR product in 1.5% agarose in 1× TAE buffer followed by staining with ethidium bromide and visualization under UV illumination. Reaction mixtures for the enzymatic digestion of amplified rRNA genes contained 100 ng of PCR product, 1× restriction buffer, 20 μg of BSA, and 10 units of restriction enzyme. The mix was adjusted to a final volume of 20 μl with water and the DNA was digested at 37° C. for 3 hours. The restriction enzymes used to evaluate model microbial communities were AluI, HhaI, HaeIII, 180 10 Coolen et al. RsaI, Msp1, HinfI, (all from Amersham Pharmacia Biotech, Uppsala, Sweden) and MvnI (Roche Applied Science, Indianapolis, Ind., USA) using buffers recommended by the manufacturers. For analysis of terminal restriction fragment length polymorphisms, 1 μl of digested PCR product was mixed with 0.5 μl internal size standards (Tamara 2500, ABI) and deionized formamide. After 3 minutes of denaturation at 95° C., the lengths of the various T-RFs were analyzed using an ABI 310 Prism automated sequencer (ABI). The various T-RFs were distinguished on the basis of differences in fluorescence.

16S rRNA gene libraries were prepared from representative samples to identify the numerically dominant constituent populations. To construct the libraries, 3 μl of PCR product was cloned in a TOPO vector (TOPO TA cloning kit, Invitrogen, San Diego, Calif., USA) using the method recommended by the manufacturer except that salts, nucleotides and primers were first removed from PCR products using Qiaquick PCR purification kits (Qiagen). One Shot E. coli cells (Invitrogen) were transformed with ligated plasmids and 50 μl of each transformation mixture was spread onto Luria-Bertani (LB) agar plates that contained X-gal, IPTG, and 50 μg/ml kanamycin. After incubation overnight at 37° C., 100 white colonies were picked, inoculated into 5 ml aliquots of LB broth that contained 50 μg/ml kanamycin. After being incubated overnight at 37° C., the cells were then harvested from each culture and plasmids were extracted. The 16S rRNA gene inserts were individually amplified by PCR using the conditions described above, and the amplified 16S rRNA gene inserts were subjected to terminal restriction fragment analysis as described above. Clones yielding T-RFs that corresponded to those in the T-RFLP profile were sequenced and the data were analyzed as described above.

From each library, the DNA sequences of approximately 200 16S rRNA clones were determined and subjected to phylogenetic analyses. The sequences of the 16S rRNA genes (positions 8 to 926) of reference strains were determined with 4 cycle sequencing reactions using the primer identified by SEQ ID NOs:1-4. Each sequencing reaction contained 4 μl of 5× Sequencing Buffer, 2 μl of the Ready Reaction Mix (Applied Biosystems Instruments, Foster City, Calif., USA), 20 ng of template DNA, and a final concentration of 0.2 μM of primer. Sterile water was added to a final volume of 20 μl. Each cycle sequencing reaction was comprised of 25 cycles and each cycle included a melting step at 96° C. (10 sec), followed by primer annealing at 50° C. (5 sec), and extension at 60° C. (4 min). Prior to sequence analysis, the products were purified using the isopropanol precipitation method as described by ABI. Sequence data were collected using an ABI Prism 310 Genetic Analyzer, and analyzed using the AutoAssembler version 2.0 software package (ABI). The 16S rRNA gene sequences obtained were matched with all sequences presently available from the databases of the Ribosomal Database Project (RDP), and GENBANK® to identify their closest relatives. Comparative analysis of the various sequences were done using the ARB program package (on the world wide web at:biol.chemie.tu-muenchen.de/pub/ARB/).

The relatedness of communities was characterized using the software program Cluster, which groups profiles based on the number, size, and abundance of 5' and 3' fragments in each profile. The software program Treeview was used to visualize the relationships between samples as dendrograms. The similarity tree was generated using average linkage clustering with an uncentered correlation metric. These applications for Windows operating systems are available on the world wide web at rana.lbl.gov/EisenSoftware.htm.

Marked differences in the diversity and species of organisms detected in the vaginal microbial communities were observed in an initial study involving five normal healthy Caucasian women between the ages of 28 and 44 (Table 1).

TABLE 1

Abundance of phylotypes in 16S rRNA gene clone libraries of normal vaginal microbial communities and percentage similarity to reference sequences.

| Phylotype* | Clones (%)† | | | | | Sequence Identity (%) |
| --- | --- | --- | --- | --- | --- | --- |
| | W-1 (n = 190) | W-2 (n = 181) | W-3 (n = 182) | W-4 (n = 176) | W-5 (n = 250) | |
| Lactobacillus crispatus | 0.0 | 98.3 | 100.0 | 0.0 | 0.0 | 97.9 ± 1.1 |
| Lactobacillus iners | 2.6 | 0.0 | 0.0 | 98.8 | 70.8 | 97.2 ± 1.8 |
| Atopobium vaginae | 92.1 | 0.0 | 0.0 | 0.0 | 5.2 | 96.8 ± 2.2 |
| Megasphaera sp. | 3.1 | 0.0 | 0.0 | 0.0 | 20.4 | 90.9 ± 5.1 |
| Letotrichia sp. | 0.0 | 0.0 | 0.0 | 0.0 | 2.4 | 93-98 |
| Gardnerella sp. | 0.0 | 0.0 | 0.0 | 0.0 | 0.8 | 93-96 |
| Peptostreptococcus sp. | 0.7 | 0.0 | 0.0 | 0.0 | 0.0 | 93 |
| Veillonella sp. | 0.0 | 0.0 | 0.0 | 0.0 | 0.4 | 90 |
| Enterococcus faecalis | 0.0 | 0.0 | 0.0 | 0.6 | 0.0 | 98 |
| Aerococcus sp. | 1.5 | 0.0 | 0.0 | 0.0 | 0.0 | 97-98 |
| Novel phylotypes | 0.0 | 1.7 | 0.0 | 0.6 | 0.0 | |

Phylogenetically related clones that on average had 90% sequence similarity to a reference strain were presumed to be of the same genus, and clones that on average had 97% sequence similarity were designated with the corresponding epithet. Clones with <90% similarity to known organisms were considered to be novel.
†W-1 to W-5 represents the women sampled.
n, Number of clones analyzed.

Species of *Lactobacillus* appeared to dominate the communities in 4 of the 5 women, whereas the community of one woman was dominated by *Atopobium* sp., and a second woman had appreciable numbers of *Atopobium* sp., *Megasphaera* sp., and *Leptotrichia* sp. None of the latter organisms have previously been shown to be common members of the vaginal ecosystem in reproductive age women. Of the women whose vaginal communities were dominated by lactobacilli, each was dominated by a single species. Two women were colonized with phylogenetically divergent clones related to *L. crispatus*, whereas two other women were colonized with clones of *L. iners* that were closely related to one another. Several bacterial populations recovered from the 16S rRNA clone libraries are not readily cultivated and may have been overlooked in previous studies. For example *L. iners* does not grow on selective media commonly used for the isolation of *Lactobacillus*, namely Mann-Rogosa-Sharp (MRS) and Rogosa media (Falsen et al., *Int J Syst Bacteriol* 49:217-221 (1999)). Likewise, *A. vaginae*, *Megasphaera* sp. and *Leptotrichia* sp. are strict anaerobes, require specialized media, and grow slowly. We suspect the sample handling and cultivation protocols normally used in clinical microbiology laboratories may have precluded the recovery of these species from vaginal samples in the past, and as a result, these genera have not been reported in studies done to define normal vaginal flora. However, it is interesting to note that *Atopobium*, *Megasphaera*, and *Leptotrichia* are all genera known to produce lactic acid as the primary product of fermentation. This suggests that the ecological function of vaginal flora, e.g., maintenance of a low pH environment that precludes the colonization and growth of pathogens and other undesirable organisms, may be conserved despite differences in community species composition.

Example 2

Categorization of Normal Vaginal Microbiota in Caucasian Women

Mid-vaginal samples from 75 normal and healthy North American Caucasian women between the ages of 13-40 years were analyzed. Samples were selected so that a total of 15 samples were drawn from each of five geographic locations: Manitoba, New Jersey, Ohio, Florida, and Arizona. Within each geographic group there was an equal number of women from each of three age groups: 13-18, 19-35, and 36-40 years old.

Vaginal specimens were collected using a sterile swab inserted into the vagina. Samples were taken near the cervix using a saline-lubricated speculum to minimize contamination by the flora of the labia during entry and withdrawal of the swab. Swabs were placed in a labeled cryovial and stored at $-70°$ C. until analysis.

A tiered approach for sample analysis was used to assess the structure of vaginal microbial communities. Statistical analyses were used to winnow the data and insure that samples representative of each community cluster (group) were carried forward to the next stage of the analysis. This reduced the total number of samples analyzed in Tiers 2 and 3 and significantly streamlined the analysis.

Analysis of Vaginal Microbial Community Structure

TIER 1: T-RFLP Analyses of 16S rRNA Gene Sequences.

In Tier 1, the T-RFLP profiles of microbial communities in each sample were determined as follows: genomic DNA was isolated from 0.5 ml aliquots of vaginal sample cell suspensions using the two-step cell lysis procedure previously described (Zhou et al., *Microbiology* 150:2565-2573 (2004)). Internal regions of the 16S rRNA genes in each sample were PCR amplified in two separate reactions using primers 8f (VIC®) and 926r (6-carboxy fluorescein, 6-FAM) and 49f (NED™) and 926r (6-FAM). The sequence of primer 49f is 5'-tnanacatgcaagtcgrrcg-3' (SEQ ID NO:5). Mixtures of the two resulting amplicons were digested separately with either MspI or HaeIII, and the products of the digestions were combined, resulting in amplification of samples using sets of primers with 3 fluorophores and digestion with 2 restriction enzymes such that each 16S rRNA gene in a sample gave rise to 6 fluorescently labeled T-RFs. The oligonucleotide primers were "universal" and theoretically annealed to the majority of 16S rRNA gene sequences in DNA sequence databases. Thus, the resulting amplicons contained regions with sequences that varied among phylogenetically distinct populations. Hence the amplicons from different populations (phylotypes) were distinguished on the basis of differences in the sizes of the restriction fragments that were produced. The restriction enzymes used have been empirically and theoretically shown to provide the greatest resolution of populations found in the human vagina on the basis of differences in the sizes of terminal restriction fragments. The profiles of fluorescently labeled terminal restriction fragments were determined using an ABI PRISM 3100 DNA Analyzer and GeneScan software as previously described by Zhou (supra).

Cluster Analysis was used to identify communities that had similar numerically abundant populations. The first step in the analysis of the T-RFLP data was to identify fragment lengths from populations that are prominent members of each microbial community. The significant fragments (peaks in the electropherograms) were used to measure the level of similarity or difference between communities. To identify "true" peaks, a threshold (baseline) was established according to the following method. The average peak area (calculated from GeneScan data) in a profile was calculated, and the peaks identified as outliers were successively removed from the dataset. The calculations were repeated using the remaining data to reduce the variation until no outliers remained. Any remaining variation represents noise alone, and the isolated peaks represent "true" peaks that can be used in the analysis. Once the peaks in all the samples were identified they were aligned so that peaks in different samples that have the same length are compared to one another. Peaks were aligned using an agglomerative clustering method based on average linkage (Johnson, *Applied multivariate methods for data analysts* (ed.) Duxbury Press (1998); Johnson & Wichern, *Applied multivariate statistical analysis*, $3^{rd}$ Edition (ed.) Prentice Hall, New Jersey (1992)). Alignment was done by first pooling, then sorting, all fragment lengths from all communities. Repeated lengths were identified and eliminated. Hierarchical clustering was performed to identify those fragments with lengths close enough to group in the same length category. The areas of peaks corresponding to fragments that clustered together within the same sample were compared. The Euclidean distances between T-RFLP profiles was used to identify similar or different communities and these were hierarchically clustered with average linkage (UPGMA). Those communities that were similar to one another formed clusters or groups. The aligned peaks resulting from processing the data were used, along with a similarity or distance measure, to create a dendrogram. Three clustering criteria were employed to identify a consensus on the number of groups in the data: the Cubical Clustering Criteria (CCC) the pseudo F; and a statistic that can be transformed to pseudo $T^2$. A 'coverage sampling approach' was implemented to identify samples representative of each kind of community for more detailed analysis in TIER 2. The proportion of species found in the most "species diverse" sample was identified and its composition (diversity) was compared to that of the entire cluster. From that point, a second community was identified that, when combined with the first, provided the largest coverage of the diversity. Additional samples were sequentially added until at least 85% of the species diversity was accounted for by the chosen samples. Note that this analysis also identified the specific samples that were carried forward to the next tier. This 'coverage sampling approach' greatly reduces the total number of samples that need to be analyzed while at the same time assuring that each cluster is adequately sampled. Typically, about 20-25% of the samples were carried forward to the next tier of the analysis.

TIER 2: Phylogenetic Analyses of Partial 16S rRNA Gene Sequences 16S rRNA.

Gene clone libraries were prepared from the samples found to be representative of each group defined in Tier 1, as previously described (Zhou et al., (2004)). Approximately 100 cloned PCR products were partially sequenced using an ABI 3730 PRISM DNA Analyzer. The data was analyzed using a suite of algorithms and software tools linked together into a "pipeline" as described above. The orientation of each sequence was determined and sequences including more than 500 bp in the 8-926 region specifically aligned (Thompson et al., *Nucleic Acids Res* 22:4673-80 (1994)) along with the sequences from the RDP database (Cole et al., *Nucleic Acids Res* 31:442-443 (2003)) found to be most closely related to each clone on the basis of BLAST searches (Altschul et al., *Nucleic Acids Res* 25:3389-3402 (1997)). The aligned sequences were used to develop a matrix of genetic distances using the Jukes and Cantor method (In *Mammalian Protein Metabolism*, Academic Press, New York (1969) which was then used to cluster the sequences using the neighbor joining method of Saitou and Nei (*Mol. Biol. Evol* 4:406-425 (1987)) as implemented in the Phylip programs "dnadist" and "neighbor" (available on the world wide web at: evolution.genetics.washington.edu/phylip.html). The resulting clusters defined operational taxonomic units (OTUs) wherein phylogenetically related clones with $\geq$90% sequence similarity to a reference strain were presumed to be members of the same genus, and clones with $\geq$97% sequence similarity were provided with the corresponding designation. Clones with $\leq$90% sequence similarity to a reference strain were determined to be novel organisms.

TIER 3: Phylogenetic Analyses of Complete 16S rRNA Gene Sequences.

The nucleotide sequences of positions 8-926 of OTUs identified in Tier 2 were determined by bidirectional sequencing. The sequences obtained were edited and assembled using ContigExpress from InforMax Vector NTI Suite 9, then aligned using CLUSTAL X (version 1.81) by considering 16S rRNA secondary structure information. Phylogenetic trees were reconstructed using the Neighbor Joining/Minimum Evolution, Maximum-Parsimony and Maximum-Likelihood algorithms using the PAUP program (Swofford, Illinois Natural History Survey, Champaign, Ill. (1998)), and Treeview 1.6.6 (on the world wide web at taxonomy.zoology.gla.ac.ck/rod.rod.htm/) was used to graphically display the evolutionary trees. Only representative sequences and sequences that are at least 90% complete were used for tree construction. Bootstrap analyses for 500 re-samplings were performed to provide confidence estimates for the tree topologies. These data indicated the phylogenetic relationships that exist among community members and provided estimates of phylotype diversity and relative abundance (that is, community composition and structure) of species in each community.

Results

Figure 2:
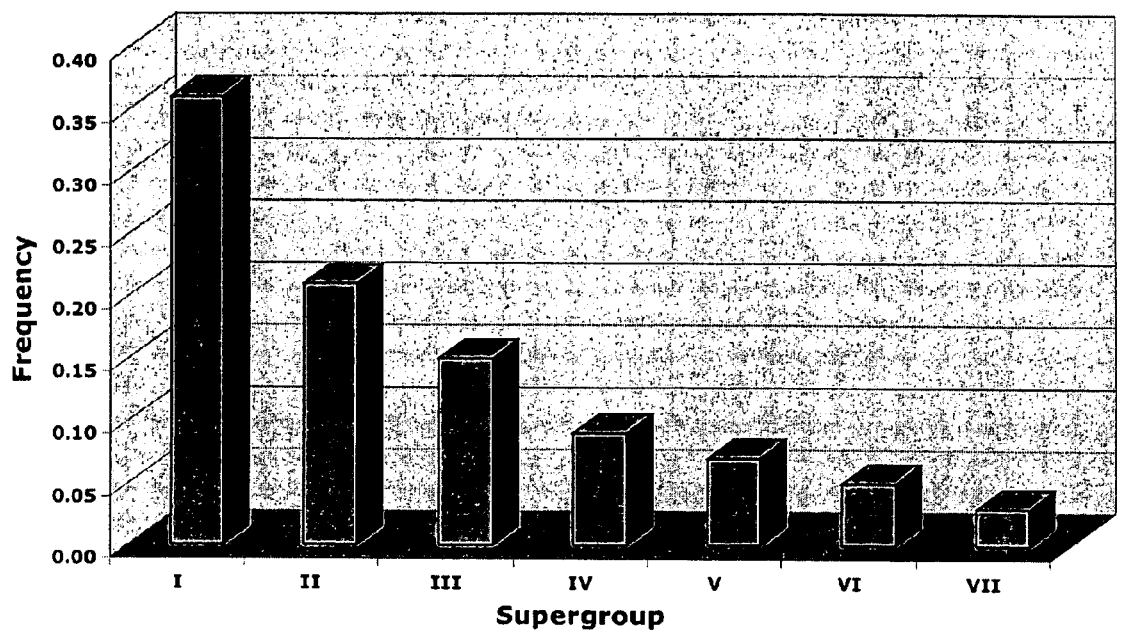
FIG. 2 is a bar graph illustrating categories of microbiota in Caucasian women.

The clustering of vaginal microbial communities based on T-RFLP data showed that 16 kinds of bacterial communities could be differentiated (FIG. 1). There were 8 major groups that included more than 2 women, and 8 groups that consisted of a single woman (which are hereafter referred to as singletons). Seven supergroups of bacterial communities account for more than 90% of the vaginal communities found in healthy Caucasian women (FIG. 2).

The supergroups defined here account for those that are most commonly encountered in Caucasian women. Statistical analyses indicated that all community types found in 3 or more of the 75 women occur in the general populace with a frequency of at least 0.10 (p=0.01). Conversely, those communities that are represented <3 times occur at a frequency of <0.10.

To identify the numerically abundant populations in each kind of community, 16S rRNA gene libraries were constructed from samples representative of each group. Typically, 2-4 libraries were prepared from samples in each major group, and libraries were prepared from all singletons. In total, 29 clone libraries were analyzed, and approximately 90 clones from each of the libraries were sequenced. Assuming the bacterial numbers in the original samples were on the order of 108 cells per ml of vaginal secretion, populations of bacteria that constitute 1-100% of a library are abundant ($\sim$10$^6$-10$^8$ cells per ml) in the corresponding sample.

Nucleotide sequences for 26 phylotypes with $\geq$97% sequence similarity to previously characterized genera and species (see Table 2), and 16 novel phylotypes with $\leq$90% sequence similarity to previously characterized genera and species, were submitted to GENBANK® and were assigned accession numbers AY995236-AY995274.

From the 16S rRNA gene sequence data obtained from the analysis of clone libraries it became apparent that the species composition of several singletons were similar to those of the larger groups (Table 2). For example, the communities of singletons O9, O10, O11, and O15 were dominated by *L. iners* and had much lower numbers of *L. crispatus* and other taxa. Since this was also characteristic of communities in group C1, these five groups were combined to form supergroup I. Likewise, groups C3 and C6 were combined to form supergroup III since communities in both groups were dominated by *L. crispatus* and *L. jensenii*, while communities in supergroup II were dominated by *L. crispatus* and had much lower numbers of *L. jensenii*. Similar logic was used to create the remaining supergroups. Overall, the results showed there were 7 principle kinds of bacterial communities in the vaginas of Caucasian women (Table 2).

Six of the seven supergroups were dominated by lactobacilli. Most often, these were *L. iners, L. crispatus, L. jensenii*, and *L. gasseri*, but *L. vaginalis*, and *L. coleohominis* were found in some communities. *L. iners* was the most common species of *Lactobacillus* in vaginal communities, and was recovered in 62/75 (83%) women and was the most abundant species in 36/75 (48%) women.

There were distinctive patterns in the occurrence of various *Lactobacillus* species in supergroups. For example, communities in Supergroups I and II, which account for 57% of the women sampled, were dominated by *L. iners* and *L. crispatus*, respectively. However, *L. iners* accounted for 90% of the clones sequenced in Supergroup I and was 100-fold more abundant than *L. crispatus*. The situation was reversed in communities of Supergroup II where *L. crispatus* comprised 88.9% of communities and greatly outnumbered *L. iners*. Vaginal communities in supergroups III, IV, VI, and VII, which represent 32% of the women sampled, were dominated by combinations of two or three species of lactobacilli whose abundances were more equal. In contrast to these, communities in supergroup V had low numbers of lactobacilli, were more diverse, and exhibited greater species evenness through the inclusion of high numbers of *A. vaginae*, Lachnospiraceae sp., *Anaerococcus* sp. *Megasphaera* sp., *Micromonas* sp., and *Dialister* sp., as well as a high percentage of novel bacteria. These novel bacteria represented ~20-30% of communities in supergroup V and all were from the order *Clostridiales*.

Communities in supergroups I and V were distinctive because they contained appreciable numbers of strictly anaerobic bacteria. They constituted 7% of the numerically dominant populations of communities in Supergroup I, and 55% of the populations in communities in supergroup V.

*Atopobium* sp. was common among the anaerobes present in these communities and found in 39% of the women sampled.

Among all of the microbial communities studied, 3 of 75 did not belong to one of the seven supergroups. Community O16 resembled supergroup VI, but the latter had 10-fold higher number of *L. crispatus*. Community O12 and O13 had high numbers of *Streptococcus* sp. and *Gemella palaticanis*, but differed from one another in that o12 also had high numbers of *Veilonella* sp. *G. palaticanis*, which is a member of the *Staphylococcaceae* and has been implicated in various infectious diseases, was also recovered in some communities in supergroups I and V.

The rank abundances of normal vaginal microbial communities are shown in FIG. 2. Statistical analyses indicated that all community types found in 3 or more of 75 women would occur in the general populace at a frequency of at least 0.10 (p=0.01).

The phylogenetic analysis of *Lactobacillus* species that were found in the vaginas of women sampled was determined by comparing the 16S rRNA gene sequences from this study to those of reference strains previously sequenced. Most lactobacilli found in the vaginal communities of Caucasian women were phylogenetically related to *L. iners, L. crispatus, L. jensenii*, and *L. gasseri*, and likely to be homofermentative, whereas *L. vaginalis* and *L. colehominis* were phylogenetically distinct and related to heterofermentative species.

TABLE 2

Species composition of vaginal communities in healthy Caucasian women.

| Phylotype‡ | Supergroup (% clones§) | | | | | | | | | | | | | | | |
|---|---|---|---|---|---|---|---|---|---|---|---|---|---|---|---|---|
| | I | | | | | II | III | | IV | V | | VI | VII | | | |
| | C1 | O9 | O10 | O11 | O15 | C2 | C3 | C6 | C4 | C5 | O14 | C7 | C8 | O12 | O13 | O16 |
| *Lactobacillus iners* | 90.2 | 93.3 | 69.4 | 96.8 | 100 | 0.5 | 0 | 0 | 59.5 | 1.7 | 0 | 2 | 51.1 | 5.6 | 3.6 | 0 |
| *Lactobacillus crispatus* | 1.1 | 1.1 | 0 | 3.2 | 0 | 88.9 | 83.1 | 50.5 | 25.7 | 0.5 | 3 | 36.1 | 29.8 | 0 | 0 | 3.3 |
| *Lactobacillus jensenii* | 1.1 | 0 | 0 | 0 | 0 | 1.5 | 12.6 | 49.5 | 2.9 | 0 | 0 | 0.7 | 19.1 | 0 | 0 | 0 |
| *Lactobacillus gasseri* | 0.2 | 0 | 0 | 0 | 0 | 0 | 3.2 | 0 | 8.9 | 21.2 | 0 | 58.9 | 0 | 0 | 0 | 93.3 |
| *Lactobacillus vaginas* | 0 | 0 | 0 | 0 | 0 | 0 | 0.7 | 0 | 0 | 0 | 0 | 0.9 | 0 | 0 | 0 | 1.7 |
| *Lactobacillus coleohominis* | 0 | 0 | 0 | 0 | 0 | 0 | 0.4 | 0 | 0 | 0 | 0 | 0 | 0 | 0 | 0 | 0 |
| *Aerococcus* sp. | 0.5 | 2.2 | 1.2 | 0 | 0 | 0 | 0 | 0 | 0.6 | 1.5 | 0 | 0 | 0 | 1.1 | 0 | 0 |
| *Anaerococcus* sp.¶ | 0 | 0 | 0 | 0 | 0 | 0 | 0 | 0 | 0 | 0.5 | 31.9 | 0 | 0 | 2.2 | 0 | 0 |
| *Atopobium vaginae*¶ | 1.6 | 0 | 5.9 | 0 | 0 | 0 | 0 | 0 | 0 | 30.7 | 4.3 | 0 | 0 | 0 | 0 | 0 |
| *Clostridium* sp.¶ | 0.5 | 0 | 0 | 0 | 0 | 0 | 0 | 0 | 0 | 0 | 0 | 0 | 0 | 0 | 0 | 0 |
| *Dialister* sp.¶ | 0 | 0 | 2.4 | 0 | 0 | 0 | 0 | 0 | 0 | 1.4 | 2.9 | 0 | 0 | 0 | 0 | 0 |
| *Enterococcus faecalis* | 0 | 0 | 0 | 0 | 0 | 0.9 | 0 | 0 | 0 | 0 | 0 | 0 | 0 | 1.1 | 0 | 0 |
| *Finegoldia magna*¶ | 0 | 1.2 | 0 | 0 | 0 | 0 | 0 | 0 | 0 | 0 | 0 | 0 | 0 | 2.2 | 0 | 0 |
| *Gardnerella vaginalis* | 0 | 0 | 0 | 0 | 0 | 0 | 0 | 0 | 0 | 0.5 | 0 | 0 | 0 | 0 | 0 | 1.7 |
| *Gemella palaticanis* | 0 | 0 | 2.4 | 0 | 0 | 0 | 0 | 0 | 0 | 0 | 4.3 | 0 | 0 | 12.2 | 4.8 | 0 |
| *Granulicatella elegans*¶ | 0 | 0 | 0 | 0 | 0 | 0 | 0 | 0 | 0 | 0 | 0 | 0 | 0 | 2.2 | 0 | 0 |
| Lachnospiraceae sp.¶ | 1.4 | 0 | 0 | 0 | 0 | 0 | 0 | 0 | 0 | 3.5 | 14.5 | 0 | 0 | 0 | 0 | 0 |
| *Leptotrichia* sp.¶ | 0 | 0 | 0 | 0 | 0 | 0 | 0 | 0 | 0 | 9.9 | 0 | 0 | 0 | 0 | 0 | 0 |
| *Megasphaera* sp.¶ | 0.2 | 2.2 | 14 | 0 | 0 | 0 | 0 | 0 | 0 | 6.5 | 1.4 | 0 | 0 | 0 | 0 | 0 |
| *Micromonas* sp. | 0 | 0 | 3.5 | 0 | 0 | 0 | 0 | 0 | 0 | 1.1 | 4.3 | 0 | 0 | 0 | 0 | 0 |
| *Peptoniphilus* sp.¶ | 0 | 0 | 0 | 0 | 0 | 0 | 0 | 0 | 0 | 0 | 4.3 | 0 | 0 | 0 | 0 | 0 |
| *Prevotella* sp. | 0 | 0 | 0 | 0 | 0 | 0 | 0 | 0 | 0 | 1 | 0 | 0 | 0 | 0 | 0 | 0 |
| *Pseudomonas* sp. | 0 | 0 | 0 | 0 | 0 | 0 | 0 | 0 | 0.6 | 0 | 0 | 0 | 0 | 0 | 0 | 0 |
| *Staphylococcus* sp. | 0 | 0 | 0 | 0 | 0 | 4.5 | 0 | 0 | 0 | 0 | 0 | 0 | 0 | 0 | 0 | 0 |
| *Streptococcus* sp. | 1.8 | 0 | 0 | 0 | 0 | 3.5 | 0 | 0 | 0.6 | 0 | 0 | 0.7 | 0 | 15.6 | 91.6 | 0 |
| *Veillonella* sp.¶ | 0 | 0 | 0 | 0 | 0 | 0 | 0 | 0 | 0 | 2.6 | 0 | 0 | 0 | 57.8 | 0 | 0 |
| Novel organisms | 1.4 | 0 | 1.2 | 0 | 0 | 0.3 | 0 | 0 | 1.2 | 17.5 | 29.1 | 0.7 | 0 | 0 | 0 | 0 |
| Numbers of women (per group) | 23 | 1 | 1 | 1 | 1 | 16 | 7 | 4 | 7 | 4 | 1 | 4 | 2 | 1 | 1 | 1 |
| Numbers of women (per supergroup) | | 27 | | | | 16 | 11 | | 7 | 5 | | 4 | 2 | | | |

‡The classification of clones was done by comparing their 16S rRNA gene sequences to those of known organisms. The genus and species names were used if the sequence similarity to a type species was >97%; the genus name only was used if the sequence similarity was <97% but >90%; and a clone was designated as novel if the sequence similarity to known organisms was <90%.
§Mean relative abundance of populations in clone libraries analyzed.
¶Strict anaerobes.

The mean sequence heterogeneity among clones of *L. crispatus*, and *L. jensenii* was greater than that of *L. iners* and *L. gasseri*, indicating that there are evolutionarily divergent subpopulations of *L. crispatus* and *L. jensenii* in vaginal communities. It should be noted that some clone sequences matched *L. crispatus* NCTC 4 (AJ242969), a reference strain that is distantly related to three other *L. crispatus* type strains. In contrast to *L. crispatus* and *L. jensenii*, the clones of *L. iners* were highly related to one another and to a single reference strain, *Lactobacillus* sp. LSPY 17362. The occurrence of a clonal lineage of *L. iners* in different women suggests there might be strong selection for specific phenotypic characteristics that are found in few strains.

The normal flora of women in supergroup V included several fastidious or strictly anaerobic microorganisms, including appreciable numbers of *Atopobium* sp., Lachnospiraceae sp., *Megasphaera* sp., *Dialister* sp. and *Anaerococcus* sp. as well as many novel bacteria that belong to the order Clostridiales. These genera are notorious for producing odoriferous compounds such as volatile fatty acids (e.g., butyrate), amines, and volatile sulfur compounds. A strong correlation between bacterial vaginosis and malodor has long been presumed, and new diagnostic tests based on amine and odor formation have been developed to quickly diagnose bacterial vaginosis. The results presented herein suggest that these tests may result in false-positives for BV. Accordingly, diagnostic criteria for BV should be amended to take these results into account.

In contrast to the prior misconception that BV results from the absence of lactobacilli, the data disclosed herein indicate that anaerobic microorganisms are common and important components of the vaginal microbial communities in some women. For example, *A. vaginae* was found in 39% of the healthy women sampled, and therefore should be considered a member of normal vaginal flora. Moreover, in vaginal communities the anaerobic bacteria Lachnospiraceae sp., *Peptoniphilus* sp., *Anaerococcus* sp., *Dialister* sp., *Finegoldia magna*, and *Granulicatella elegans* were reported for the first time to be constituents of the normal vaginal flora. These findings illustrate that in some cases (e.g., supergroup V), anaerobic bacteria may outnumber lactobacilli, indicating that these species contribute to the "normal" flora.

Example 3

Categorization of Normal Vaginal Microbiota in African-American Women

Disparities in the incidence of BV and sexually transmitted diseases among racial groups have been well documented. BV occurs in 17-19% of all female patients attending family practice clinics. However the incidence among minority (Black and Mexican-American) women exceeds 50%. To improve diagnostic and patient management capabilities, the identity of the dominant bacterial populations of healthy Black women using cultivation-independent methods was determined and compared to the bacterial populations in healthy White women.

Seventy randomly selected vaginal samples obtained from (self-declared) Black subjects were selected for analysis. Fifteen samples from four geographic sites in the United States were chosen (Cincinnati, Ohio; East Brunswick, N.J.; St. Petersburg, Fla. and Scottsdale, Ariz.), and within each geographic group there were equal numbers of women from each of three age groups: 13-18, 19-35, and >35-40 years old. A total of 10 samples were included from the Canadian site (Winnipeg, Manitoba). Three (3) were from the 13-18 age group, five were from the 19-35 age group and 2 were from the >35-40 year age group.

Samples were obtained and analyzed as described in the previous Example. Supergroups were defined based on a subjective assessment of similarities in the composition and relative abundance of phylotypes in the various groups. The phylogenetic relationships of vaginal bacterial populations in the order Clostridiales were determined by comparison to reference sequences obtained from GENBANK®.

Results

Figure 3:
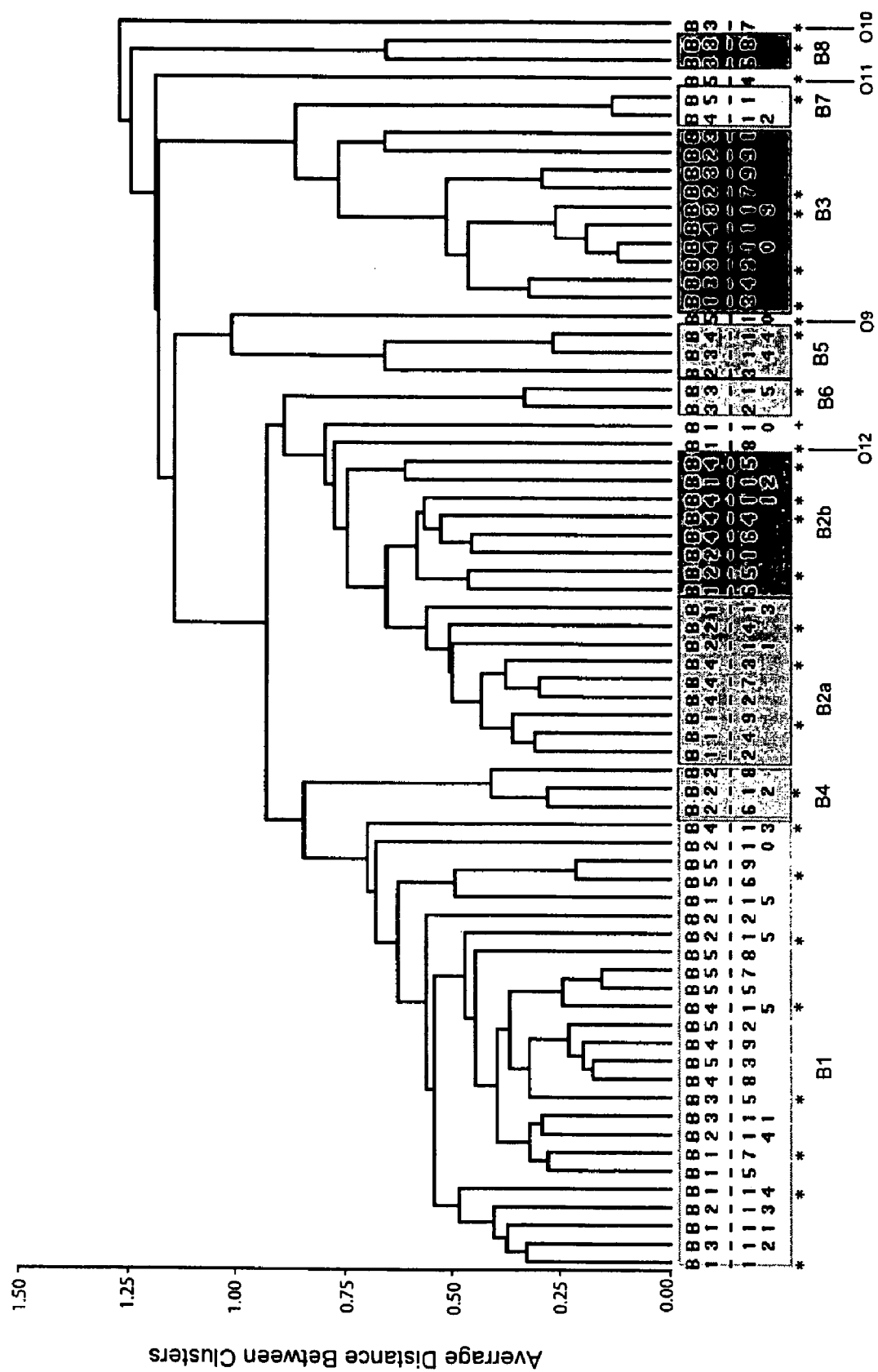
FIG. 3 is a dendrogram illustrating the relationships between normal categories of vaginal microbiota in African-American women.

The data from T-RFLP analysis of 16S rRNA genes were subjected to cluster analysis to identify related vaginal microbial communities. Twelve kinds of bacterial communities could be differentiated (FIG. 3). The composition of communities representative of each group were determined by phylogenetic analysis of cloned 16S rRNA sequences (Table 3) and similar groups were combined into supergroups based on a subjective assessment of similarities in the composition and relative abundance of phylotypes in the various groups. There were five major supergroups represented by ≧2 women, and 4 individual women whose communities differed from each other and those in the supergroups. Statistical analyses indicated that all community types found in the general populations with a frequency of at least 0.085 were represented by groups that contain 2 or more women (p=0.01).

The vaginal communities of most African-American women (64%) were dominated by various species of *Lactobacillus* (Table 1). As with Caucasian women, the most common community type was supergroup I, which was dominated *L. iners*. There were two supergroups found in African-American women that were not present in Caucasian women, namely VIII and IX, which were dominated by *L. gasseri* and a novel uncultured bacterium, respectively. The novel bacterium had <90% 16S rRNA gene sequence similarity to known organisms, and therefore it represents a previously undescribed lineage of bacteria. The phylotype is related to organisms found in the order Clostridiales and the class Lachnospiraceae, and is closely related (98% similarity) to another uncultured bacterial clone 7200-2c13Sm (GENBANK® Accession No. AY471619) that was also recovered from vaginal swab sampled by Ferris et al. (GENBANK®).

Figure 4:
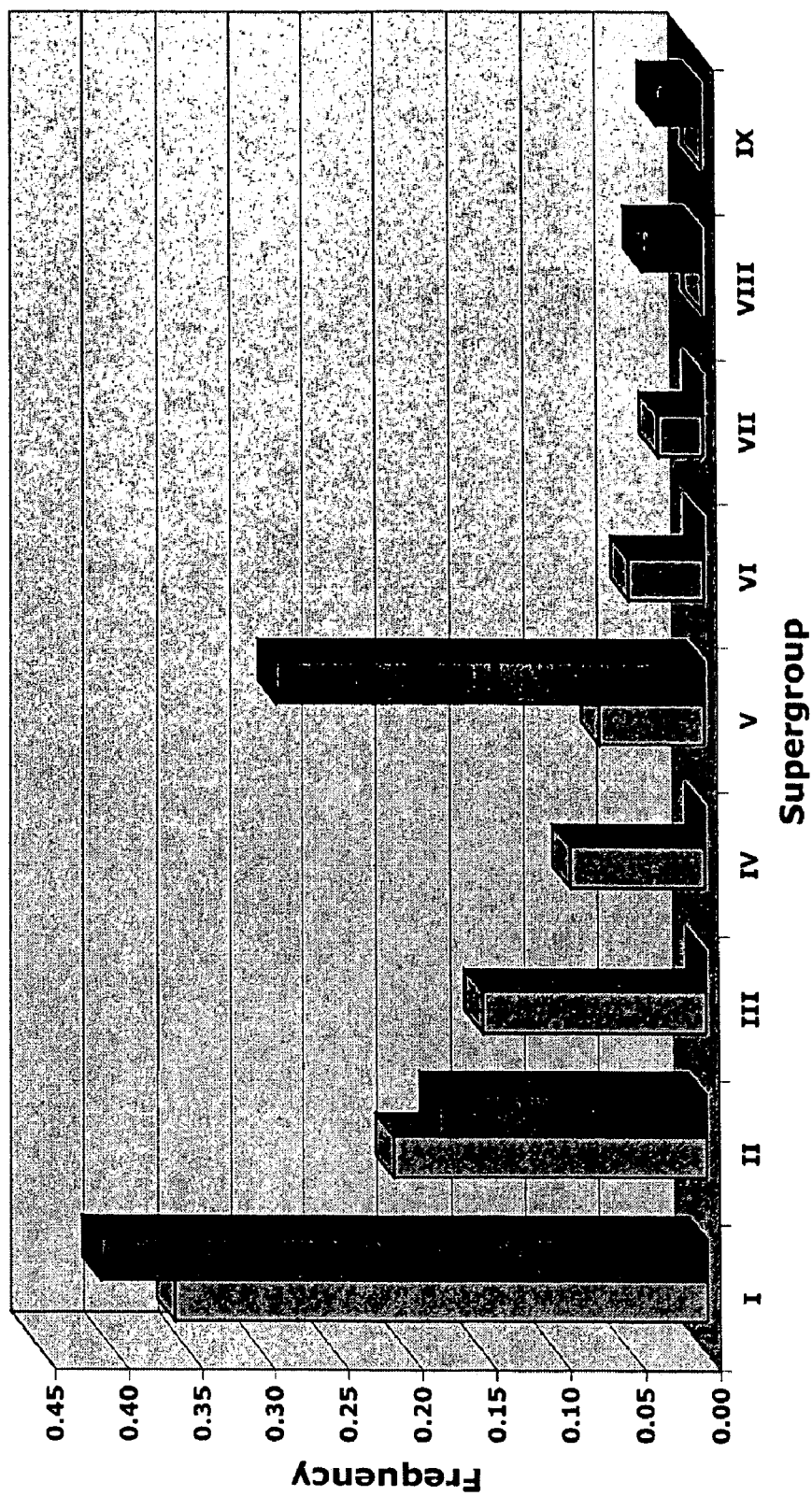
FIG. 4 is a bar graph illustrating categories of microbiota in African-American women an and comparing categories between Caucasian and African American women. Left hand bars represent Caucasian women, whereas right hand bars represent African-American women.

The rank abundance of community types in African-American and Caucasian women are shown in FIG. 4. Three findings are readily apparent. First, communities akin to supergroup V were four times more common in African-American women than in Caucasian women. Second, communities dominated by roughly equal numbers of more than one species of *Lactobacillus* (supergroups III, IV, VI, and VII) were not found in African-American women. Third, only three of the seven supergroups (I, II and V) found in Caucasian women were also found in African-American women. Thus, a significant fraction of African-American women have vaginal communities that differ in bacterial composition from those of Caucasian women.

TABLE 3

Species composition of vaginal communities in healthy Black women.

| | Supergroup (% clones§) | | | | | | | | | | | | |
|---|---|---|---|---|---|---|---|---|---|---|---|---|---|
| | I | | V | | | II | | VIII | IX | | | | |
| Phylotype‡ | B1 | B4 | B2a | B8 | B2b | B3 | B7 | B5 | B6 | O9 | O10 | O11 | O12 |
| *Lactobacillus iners* | 75.4 | 89.5 | 20.2 | 0 | 0.9 | 0.7 | 0 | 0 | 0 | 0 | 0 | 0 | 0 |
| *Lactobacillus crispatus* | 2.1 | 0 | 0 | 0 | 0 | 97.7 | 97.8 | 0 | 0 | 0 | 0 | 0 | 0 |
| *Lactobacillus jensenii* | 0 | 1.5 | 0 | 0 | 0 | 1.7 | 2.2 | 0 | 0 | 7.3 | 0 | 80.9 | 0 |
| *Lactobacillus gasseri* | 0.3 | 3 | 0 | 0 | 0 | 0 | 0 | 98.8 | 0 | 40 | 0 | 0 | 0 |
| *Lactobacillus vaginas* | 0 | 0 | 0 | 0 | 0 | 0 | 0 | 0 | 0 | 0 | 0 | 0 | 0 |
| *Lactobacillus coleohominis* | 0 | 4.5 | 0 | 0 | 0 | 0 | 0 | 0 | 0 | 5.5 | 0 | 0 | 0 |
| *Lactobacillus salivarius*¶ | 0.1 | 0 | 0 | 0 | 0 | 0 | 0 | 0 | 0 | 0 | 0 | 0 | 0 |
| *Actinobacculum* sp.¶ | 0.2 | 0 | 0 | 0 | 0 | 0 | 0 | 0 | 0 | 0 | 0 | 0 | 0 |
| *Aerococcus* sp. | 1.6 | 0 | 0 | 1.1 | 0.6 | 0 | 0 | 0 | 0 | 0 | 0 | 0 | 0 |
| *Anaerobranca* sp.¶ | 0.2 | 0 | 0 | 0 | 2.7 | 0 | 0 | 0 | 0 | 0 | 0 | 0 | 0 |
| *Anaerococcus* sp. | 0.3 | 0 | 1.9 | 1.1 | 0 | 0 | 0 | 0 | 0 | 0 | 0 | 0 | 0 |
| *Atopobium vaginae* | 1.5 | 1.5 | 21 | 27.8 | 3.8 | 0 | 0 | 1.2 | 3.5 | 0 | 0 | 0 | 1.2 |
| *Catonella* sp.¶ | 0 | 0 | 0 | 0 | 0 | 0 | 0 | 0 | 0 | 0 | 0 | 2.4 | 0 |
| *Clostridium* sp. | 0 | 0 | 0 | 0 | 0.3 | 0 | 0 | 0 | 0 | 0 | 0 | 0 | 0 |
| *Corynebacterium* sp.¶ | 0 | 0 | 0 | 0 | 0 | 0 | 0 | 0 | 0 | 3.6 | 0 | 0 | 0 |
| *Dialister* sp. | 0 | 0 | 2.7 | 3.3 | 3.3 | 0 | 0 | 0 | 0 | 0 | 0 | 0 | 4.8 |
| *Eggerthella hongkongensis*¶ | 0 | 0 | 0.8 | 0 | 0 | 0 | 0 | 0 | 0 | 0 | 0 | 0 | 0 |
| *Escherichia coli*¶ | 0 | 0 | 0 | 0 | 0 | 0 | 0 | 0 | 0 | 0 | 27.6 | 0 | 0 |
| *Finegoldia magna* | 0 | 0 | 0 | 2.3 | 0 | 0 | 0 | 0 | 0 | 0 | 0 | 1.2 | 0 |
| *Gardnerella vaginalis* | 0 | 0 | 0 | 0 | 0 | 0 | 0 | 0 | 0 | 9.1 | 0 | 0 | 0 |
| *Gemella palaticanis* | 0.4 | 0 | 0 | 7.8 | 1.7 | 0 | 0 | 0 | 0 | 0 | 0 | 0 | 15.7 |
| *Lachnospiraceae* sp. | 0 | 0 | 0.8 | 0 | 0 | 0 | 0 | 0 | 0 | 0 | 0 | 0 | 0 |
| *Megasphaera* sp. | 1.8 | 0 | 2.1 | 12.2 | 9.5 | 0 | 0 | 0 | 10.3 | 0 | 0 | 0 | 0 |
| *Micromonas* sp. | 0.6 | 0 | 9.6 | 6.7 | 8.5 | 0 | 0 | 0 | 4.6 | 0 | 0 | 0 | 1.2 |
| *Mobiluncus mulieris*¶ | 0.2 | 0 | 0 | 0 | 0 | 0 | 0 | 0 | 2.3 | 0 | 0 | 0 | 0 |
| *Mycoplasma* sp.¶ | 0 | 0 | 0 | 0 | 0.6 | 0 | 0 | 0 | 0 | 0 | 0 | 0 | 74.5 |
| *Peptococcus niger*¶ | 0 | 0 | 0.4 | 0 | 0 | 0 | 0 | 0 | 0 | 0 | 0 | 0 | 0 |
| *Peptoniphilus* sp. | 0.5 | 0 | 1.3 | 1.1 | 5.1 | 0 | 0 | 0 | 3.5 | 0 | 0 | 0 | 0 |
| *Peptostreptococcus* sp.¶ | 0 | 0 | 5.7 | 0 | 15.5 | 0 | 0 | 0 | 0 | 0 | 0 | 0 | 2.4 |
| *Prevotella* sp. | 0 | 0 | 0 | 0 | 0.6 | 0 | 0 | 0 | 0 | 0 | 0 | 2.4 | 0 |
| *Pseudomonsa* sp. | 0.2 | 0 | 0 | 0 | 0 | 0 | 0 | 0 | 0 | 0 | 0 | 0 | 0 |
| *Shigella* sp.¶ | 0 | 0 | 0 | 0 | 0 | 0 | 0 | 0 | 0 | 0 | 71.1 | 0 | 0 |
| *Streptococcus* sp. | 6.1 | 0 | 0 | 0 | 0 | 0 | 0 | 0 | 0 | 34.5 | 0 | 11.9 | 0 |
| *Veillonella* sp. | 0.3 | 0 | 0.8 | 0 | 0 | 0 | 0 | 0 | 0 | 0 | 0 | 0 | 0 |
| Uncultured bacterium† | 0 | 0 | 0 | 0 | 0.6 | 0 | 0 | 0 | 72.4 | 0 | 0 | 0 | 0 |
| Novel bacteria | 8.4 | 0 | 32.7 | 36.6 | 46.4 | 0 | 0 | 0 | 3.4 | 0 | 1.3 | 1.2 | 0 |
| Numbers of women (per group) | 25 | 3 | 9 | 2 | 8 | 10 | 2 | 3 | 2 | 1 | 1 | 1 | 1 |
| Numbers of women (per supergroup) | 28 | | 19 | | | 12 | | 3 | 2 | 4 | | | |

‡The classification of clones was done by comparing their 16S rRNA gene sequences to those of known organisms. The genus and species names were used if the sequence similarity to a type species was >97%; the genus name only was used if the sequence similarity was <97% but >90%; and a clone was designated as novel if the sequence similarity to known organisms was <90%.
§Mean relative abundance of populations in clone libraries analyzed.
¶Not found in Caucasian women.
†The uncultured bacterium is a members of the order Clostridiales, but was unrelated to any previous cultured organism.

Two subgroups could be distinguished in supergroup V. Communities in both subgroups had fewer lactobacilli than other supergroups, and they were exclusively *L. iners*. Group B2a had roughly equal numbers of *L. iners* and *A. vaginae* and each constituted about 20% of the community, while group B2b had 10-fold fewer *L. iners* than group B2a, and reduced numbers of *A. vaginae* (Table 3). Communities of both subgroups had appreciable numbers of strictly anaerobic bacteria including *Atopobium, Dialister, Megasphaera, Peptinophilus, Micromonas*, and an assortment of phylotypes related to organisms in the order Costridiales, but their abundance in women of subgroup B2b were generally higher.

A significant fraction (67%) of Black women from three of the five supergroups (I, V, and IX) had high numbers of novel phylotypes in their vaginal communities (Table 3). These bacterial populations were all strict anaerobes that belong to the order Clostridiales, and the diversity among them was striking. These populations were related to organisms in four major families namely the Lachnospiraceae, Acidaminococcaceae, Peptostreptococcaceae, and Clostridiaceae. The 16S rRNA gene sequences of the 16 populations were <90% similar to previously characterized genera.

Among the microbial communities observed, 4 of 69 were "singletons". Community O11 was dominated by *L. jensenii*, which accounted for 80.9% of the clones analyzed, and there were also high numbers of *Streptococcus* sp., *Catenella* sp., *Prevotella* sp. and *Finegoldia* sp. Singeltons O9, O10 and O12 differed from other communities; all had high numbers of *Gardnerella vaginalis, Escherichia coli, Shigella* sp., and *Mycoplasma* sp. These three women may suffer from vaginal infections that were overlooked, or may have transiently high numbers of organisms of fecal origin.

These findings indicate there were significant differences in the vaginal flora between African-American and Caucasian women. First, the incidence of vaginal communities in which lactobacilli were not dominant (<10% of the clones recovered) was higher in Black women as compared to Caucasian women (19% versus 4%). Secondly, communities dominated by *Atopobium* and various species related to Clostridiaceae occurred in 32% of the Black women sampled, but were dominant in only 10% of Caucasian women. Indeed, Clostridiaceae were common among Black women and occurred in more than 5% of the clones in 75% of Black women, but in only 10% of Caucasian women. Third, communities dominated by roughly equal numbers of more than one species of *Lactobacillus* (supergroups III, IV, VI, and VII) were not found in Black women, but were common and present in 32% of Caucasian women. Finally, supergroups VIII and IX were only found in Black women, and Black women exhibited only three of the seven supergroups (I, II and IV) found in Caucasian women.

Epidemiology studies have clearly shown that Black women have a higher prevalence of BV, reproductive tract infections, heterosexually transmitted STDs and HIV, and preterm deliveries. It is possible that certain kinds of vaginal microbial communities in Black women might be more easily upset by disturbances than microbial communities found in White women. Alternatively, certain kinds of vaginal communities that are more common or only found in Caucasian women may be more resilient to such common disturbances as menses, sexual intercourse, douching, and contraceptive practices. Supergroups V, VIII, and IX are obvious candidates since they are more common or exclusively occur in Black women.

Many healthy Black women hosted novel bacteria related to the Clostridiaceae. These are likely to be fastidious strict anaerobes, and probably not readily recovered using cultivation methods commonly used in studies of vaginal flora. Clostridiaceae are notorious for the production of malodorous metabolites, including amines and short-chain fatty acids. The discovery that they are constituents of normal vaginal communities suggests that vaginal odor may not be a reliable indicator of bacterial vaginosis or any other disease condition. This has important implications for the diagnosis of BV and does not support proposed criteria for the clinical diagnosis of bacterial vaginosis that are, in part, based on a correlation between bacterial vaginosis and malodor. Similarly, diagnostic procedures for BV based on the occurrence of bacteria that have cellular morphologies that are characteristic of lactobacilli are likely to be unreliable since high numbers of bacteria other than species of *Lactobacillus* are common in healthy women. The false positives from these diagnostic tests, or the treatment of patients based solely on complaints of odor, results in the unnecessary treatment of patients with antibiotics. Not only is this costly, but it could lead to disturbances of intestinal or vaginal flora and cause problems that otherwise would not have occurred. The findings disclosed herein indicate that diagnostic criteria for BV should be amended to take into account the occurrence of organisms that are morphologically distinct from lactobacilli or normally produce odiferous metabolites.

*Atopobium* sp. was commonly encountered as a member of the vaginal communities. While *A. vaginae* has rarely been isolated from any environment, it has been recovered from vagina of a healthy individual in Sweden (Rodriguez et al. *Int J Syst Bacteriol* 49:1573-1576, 1999). Species of *Atopobium* may have been previously overlooked because they are fastidious, obligate anaerobes that grow slowly and form pinpoint colonies on agar media. While *Anaerococcus* sp., *Megasphaera* sp., and members of the Lachnospiraceae and Clostridiaceae families are less fastidious, they are strict anaerobes and would not be recovered from samples by using the cultivation methods that have been commonly used in previous studies of vaginal flora, or routinely used in clinical microbiology laboratories. Recent studies have used specific PCR primers to demonstrate the presence of *Atopobium* in women. For example, Ferris et al (*J Clin Microbiol* 42:5892-5894, 2004) reported that *A. vaginae* was detected in a significant portion (55%) of the 20 BV-positive patients in the cohort and present in only 2 of 24 women with normal vaginal Gram strains. Burton et al. (*J Clin Microbiol* 42:1829-1831, 2004) made a survey of 35 postmenopausal women, *A. vaginae* was detected in 44% with BV (asymptomatic bacteria vaginosis) but not in any subjects deemed healthy. These findings have led investigators to suggest that *Atopobium* may be a causative agent of BV. However, the present disclosure contradicts the previous findings. *Atopobium* was found in 77% of Black women and in 39% of Caucasian that were healthy and showed no clinical symptoms of BV. The high incidence of *Atopobium* among women in both racial groups suggests that it is a common, and heretofore unrecognized member of the vaginal normal flora in a large fraction of women.

Example 4

Diagnostic Reagents and Kits

Exemplary probes and primers for detecting the predominant species of microorganisms in the above describe categories of normal vaginal microbiota are provided in Table 4. The primers and probes are utilized to detect individual species or groups of microorganism using routine hybridization and amplification methodologies. Optionally, a plurality of primers and/or probes can be employed together to generate a microbial profile useful for assigning a microbial profile to a normal category of vaginal microbiota. Optionally, the primers and/or probes are provided as a kit, which can also include additional reagents for the preparation of samples, performance of reactions and/or detection of microorganisms. One example of a kit includes an array of species specific probes, such as probes selected from SEQ ID NOs:6-23. For example, the probes can be provided arrayed on substrate or matrix, such as a chip or slide. In one embodiment, the probes are arrayed on a dipstick.

In view of the many possible embodiments to which the principles of our invention may be applied, it should be recognized that the illustrated embodiments are only examples of the invention and should not be taken as a limitation on the scope of the invention. Rather, the scope of the invention is defined by the following claims. We therefore claim as our invention all that comes within the scope and spirit of these claims.

TABLE 4

Diagnostic Probes and Primers

| Organism | Orientation | Sequence (5'-3') |
|---|---|---|
| *Atopobium vaginae* (species specific) | forward | AGA GTT TGA TCM TGG CTC AG (SEQ ID NO:1) |
| | reverse | TTC TGC TCG CGC AGT AGC AG (SEQ ID NO:6) |
| Atopobium (group specific) | forward | AGA GTT TGA TCM TGG CTC AG (SEQ ID NO:1) |
| | reverse | CTC CTG ACC TAA CAG ACC (SEQ ID NO:7) |
| | forward | TCT TAA AAG TGC GGG GCT TA (SEQ ID NO:8) |
| Megasphaera (group specific) | reverse | CCG TCA ATT CCT TTR AGT TT (SEQ ID NO:3) |
| | forward | AGA GTT TGA TCM TGG CTC AG (SEQ ID NO:1) |
| *Gardnerella vaginalis* (species-specific) | reverse | AGA CGG CTC CAT CCC AAA AGG GTT (SEQ ID NO:9) |
| | forward | GCG GTC CGG CCG GGA ACT CAA A (SEQ ID NO:10) |
| Enteric bacteria (group specific) | reverse | CAT CTG GGC ACA TCC GAT GG (SEQ ID NO:11) |
| | forward | TGT AGA CTG GGA TAA CAG AG (SEQ ID NO:12) |
| Leptotrichia (group specific) | reverse | CCG TCA ATT CCT TTR AGT TT (SEQ ID NO:3) |
| | forward | AGA GTT TGA TCC TGG CTC AG (SEQ ID NO:13) |
| Streptococcus (group specific) | reverse | GTA CCG TCA CAT TGT GAA TTT TCC (SEQ ID NO:14) |
| | forward | TAA CTG TAC ACG TCT TGA CGG (SEQ ID NO:15) |
| Staphylococcus (group specific) | reverse | CCG TCA ATT CCT TTR AGT TT (SEQ ID NO:3) |
| | forward | GTA ATA CAT AGG TCG CAA GCG TTA TC (SEQ ID NO:16) |
| Mycoplasma (group specific) | reverse | CAC CAT CTG TCA CTC TGT TAA CCT C (SEQ ID NO:17) |
| *Mycoplasma genitalium* (species specific) | forward | GTA ATA CAT AGG TCG CAA GCG TTA TC (SEQ ID NO:18) |
| | reverse | TCG GAG CGA TCC CTT CGG T (SEQ ID NO:19) |
| | forward | GTA ATA CAT AGG TCG CAA GCG TTA TC (SEQ ID NO:20) |
| *Mycoplasma hominis* (species specific) | reverse | GAC ACT AGC AAA CTA GAG TTA G (SEQ ID NO:21) |
| | forward | AGA GTT TGA TCM TGG CTC AG (SEQ ID NO:1) |
| *Lactobacillus iners* (species specific) | reverse | ACT GGG GTG AAG TCG TAA CA (SEQ ID NO:22) |
| | forward | CCG GAT AAG AAA GCA GAT CG (SEQ ID NO:23) |
| *Lactobacillus crispatus* (species specific) | reverse | CCG TCA ATT CCT TTR AGT TT (SEQ ID NO:3) |

We claim:

1. A method of defining one or more normal vaginal microbial communities, the method comprising:

obtaining a plurality of single vaginal samples, wherein each single sample comprises vaginal microorganisms obtained from a female without vaginal pathology;

using analytical laboratory techniques to obtain a plurality of microbial profiles, wherein each microbial profile is obtained from the single sample of vaginal microorganisms obtained from a female without vaginal pathology;

identifying a plurality of consensus profiles from among the plurality of microbial profiles, thereby defining a plurality of normal vaginal microbial communities, wherein the plurality of consensus profiles comprise the seven supergroups shown in Table 2; and providing the plurality of consensus profiles to a user.

2. The method of claim 1, wherein the microbial profiles are provided by a culture-independent method.

3. The method of claim 2, wherein the culture-independent method comprises:

preparing at least one nucleic acid sample from at least one species of microbiota present in the vaginal sample, the at least one nucleic acid sample comprising at least one molecular indicator of identity; and characterizing the at least one nucleic acid sample based on restriction endonuclease cleavage patterns of molecular indicators of identity, thereby providing the plurality of microbial profiles.

4. The method of claim 1 where the female is a female human.

5. The method of claim 1, wherein identifying the plurality of consensus profiles from among the plurality of microbial profiles is by evaluating restriction endonuclease fragment patterns of the plurality of microbial profiles.

6. The method of claim 1, wherein identifying the plurality of consensus profiles from among the plurality of microbial profiles is by cluster analysis of the plurality of microbial profiles.

7. The method of claim 1, further comprising:
identifying single samples that when combined account for at least 85% of species diversity of microbial communities that define each of the plurality of consensus profiles; and
determining which microbes are present in the single samples.

8. The method of claim 7, further comprising:
determining presence and prevalence of particular microorganisms in a test sample; and
assigning the test sample to a class of microbial community based on the presence and prevalence of particular microorganisms in the test sample.

9. The method of claim 1, wherein the providing the plurality of consensus profiles to a user comprises providing the plurality of consensus profiles to a user for assigning a subject to a consensus profile.

10. A method of defining one or more normal vaginal microbial communities, the method comprising:
obtaining a plurality of single vaginal samples, wherein each single sample comprises vaginal microorganisms obtained from a female without vaginal pathology;
using analytical laboratory techniques to obtain a plurality of microbial profiles, wherein each microbial profile is obtained from the single sample of vaginal microorganisms obtained from a female without vaginal pathology;
identifying a plurality of consensus profiles from among the plurality of microbial profiles, thereby defining a plurality of normal vaginal microbial communities, wherein the plurality of consensus profiles comprises the five supergroups shown in Table 3; and
providing the plurality of consensus profiles to a user.

11. The method of claim 10, wherein the plurality of microbial profiles are obtained by:
preparing a nucleic acid sample from the one or more microorganisms, wherein the nucleic acid sample comprises at least one molecular indicator of identity; and
characterizing the at least one nucleic acid sample based on restriction endonuclease cleavage patterns of molecular indicators of identity, thereby providing the plurality of microbial profiles.

12. The method of claim 11, further comprising identifying relatedness within the plurality of microbial profiles by using a clustering algorithm.

13. The method of claim 12, wherein clustering patterns are evaluated by a statistical method selected from a cubical clustering criterion analysis, a pseudo F analysis, a pseudo $T^2$ test, or combinations thereof.

14. The method of claim 11, wherein the at least one molecular indicator of identity is a polymorphic nucleotide sequence.

15. The method of claim 14, wherein the polymorphic nucleotide sequence comprises an rRNA gene.

16. The method of claim 15, wherein the polymorphic nucleotide sequence comprises a 16S rRNA gene.

17. The method of claim 11, wherein the at least one molecular indicator of identity is a phylogenetically informative gene.

18. The method of claim 10, wherein the microbial profiles are provided by a culture-independent method.

19. The method of claim 18, wherein the culture-independent method comprises:
preparing at least one nucleic acid sample from at least one species of microbiota present in the vaginal sample, the at least one nucleic acid sample comprising at least one molecular indicator of identity; and
characterizing the at least one nucleic acid sample based on restriction endonuclease cleavage patterns of molecular indicators of identity, thereby providing the plurality of microbial profiles.

20. The method of claim 10, wherein the female is a female human.

21. The method of claim 10, wherein identifying the plurality of consensus profiles from among the plurality of microbial profiles is by evaluating restriction endonuclease fragment patterns of the plurality of microbial profiles.

22. The method of claim 10, wherein identifying the plurality of consensus profiles from among the plurality of microbial profiles is by cluster analysis of the plurality of microbial profiles.

23. The method of claim 10, further comprising:
identifying single samples that when combined account for at least 85% of species diversity of microbial communities that define each of the plurality of consensus profiles; and
determining which microbes are present in the single samples.

24. The method of claim 23, further comprising:
determining presence and prevalence of particular microorganisms in a test sample; and
assigning the test sample to a class of microbial community based on the presence and prevalence of particular microorganisms in the test sample.

25. The method of claim 10, wherein the providing the plurality of consensus profiles to a user comprises providing the plurality of consensus profiles to a user for assigning a subject to a consensus profile.

26. The method of claim 1, wherein the plurality of microbial profiles are obtained by:
preparing a nucleic acid sample from the one or more microorganisms, wherein the nucleic acid sample comprises at least one molecular indicator of identity; and
detecting differences in the at least one molecular indicator of identity based upon their restriction endonuclease cleavage patterns, thereby providing one of the plurality of microbial profiles.

27. The method of claim 26, further comprising identifying relatedness within the plurality of microbial profiles by using a clustering algorithm.

28. The method of claim 27, wherein clustering patterns are evaluated by a statistical method selected from a cubical clustering criterion analysis, a pseudo F analysis, a pseudo $T^2$ test, or combinations thereof.

29. The method of claim 26, wherein the at least one molecular indicator of identity is a polymorphic nucleotide sequence.

30. The method of claim 29, wherein the polymorphic nucleotide sequence comprises an rRNA gene.

31. The method of claim 30, wherein the polymorphic nucleotide sequence comprises a 16S rRNA gene.

32. The method of claim 26, wherein the at least one molecular indicator of identity is a phylogenetically informative gene.

* * * * *